US009861768B2

(12) United States Patent
Kataoka et al.

(10) Patent No.: US 9,861,768 B2
(45) Date of Patent: Jan. 9, 2018

(54) PHARMACEUTICAL INJECTION DEVICE, AND PHARMACEUTICAL MANAGEMENT SYSTEM

(71) Applicant: Panasonic Healthcare Holdings Co., Ltd., Minato-ku, Tokyo (JP)

(72) Inventors: Yoshihiro Kataoka, Ehime (JP); Tooru Aoki, Ehime (JP); Seiji Kikuchi, Ehime (JP); Kenji Murakami, Ehime (JP); Takahiko Tanida, Ehime (JP); Katsumi Nakanishi, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 89 days.

(21) Appl. No.: 15/101,930

(22) PCT Filed: Jan. 23, 2015

(86) PCT No.: PCT/JP2015/051830
§ 371 (c)(1),
(2) Date: Jun. 6, 2016

(87) PCT Pub. No.: WO2015/115326
PCT Pub. Date: Aug. 6, 2015

(65) Prior Publication Data
US 2016/0310680 A1    Oct. 27, 2016

(30) Foreign Application Priority Data

Jan. 28, 2014 (JP) .................................. 2014-013407

(51) Int. Cl.
*G01K 13/00* (2006.01)
*G01K 1/00* (2006.01)
(Continued)

(52) U.S. Cl.
CPC ............ *A61M 5/5086* (2013.01); *A61M 5/20* (2013.01); *A61M 5/3146* (2013.01);
(Continued)

(58) Field of Classification Search
USPC .................................................. 374/141, 208
See application file for complete search history.

(56) References Cited

U.S. PATENT DOCUMENTS 6,302,855 B1    10/2001  Lav et al.
8,398,602 B2    3/2013   Ilo et al.
(Continued)

FOREIGN PATENT DOCUMENTS

EP    1 079 876 B1    3/2001
EP    1 531 886 B1    5/2005
(Continued)

OTHER PUBLICATIONS

The Search Report from the corresponding International Patent Application No. PCT/JP2015/051830 dated Apr. 21, 2015.
(Continued)

*Primary Examiner* — Mirellys Jagan
(74) *Attorney, Agent, or Firm* — Shinjyu Global IP

(57) ABSTRACT

A pharmaceutical injection device may comprise a main body case in the interior of which a pharmaceutical syringe can be mounted; a drive means that is provided inside the main body case and pushes out the pharmaceutical inside the pharmaceutical syringe through a syringe needle; a cover that opens and closes an opening on the side of the main body case where the syringe needle is mounted; an outside air temperature sensor that measures a first temperature, which is the temperature outside the main body case; a display component; and a controller that controls the drive means and the display component and acquires the first temperature at predetermined intervals. When the cover is (Continued)

closed, the controller causes the display component to display information about the storage state of the pharmaceutical in the mounted pharmaceutical syringe on the basis of the first temperature.

24 Claims, 28 Drawing Sheets

(51) Int. Cl.
    *A61M 5/50*     (2006.01)
    *A61M 5/20*     (2006.01)
    *A61M 5/31*     (2006.01)
    *A61M 5/32*     (2006.01)

(52) U.S. Cl.
    CPC .......... *A61M 5/326* (2013.01); *A61M 5/3234* (2013.01); *A61M 5/3287* (2013.01); *A61M 2005/206* (2013.01); *A61M 2205/18* (2013.01); *A61M 2205/276* (2013.01); *A61M 2205/3368* (2013.01); *A61M 2205/3569* (2013.01); *A61M 2205/50* (2013.01); *A61M 2205/502* (2013.01); *A61M 2205/583* (2013.01)

(56) References Cited

U.S. PATENT DOCUMENTS

| | | | |
|---|---|---|---|
| 9,707,156 B2* | 7/2017 | Wengreen | ............... A61J 1/165 |
| 2002/0013522 A1 | 1/2002 | Lav et al. | |
| 2004/0176720 A1 | 9/2004 | Kipfer | |
| 2005/0177137 A1 | 8/2005 | Kipfer | |
| 2007/0244412 A1 | 10/2007 | Lav et al. | |
| 2008/0125700 A1 | 5/2008 | Moberg et al. | |
| 2009/0128330 A1* | 5/2009 | Monroe | ................ A61M 5/002 340/568.1 |
| 2011/0218502 A1* | 9/2011 | Iio | ......................... A61M 5/003 604/264 |
| 2011/0319813 A1 | 12/2011 | Kamen et al. | |
| 2012/0035543 A1 | 2/2012 | Kamen et al. | |
| 2013/0175192 A1 | 7/2013 | Iio et al. | |
| 2014/0330199 A1 | 11/2014 | Murakami et al. | |
| 2015/0165121 A1 | 6/2015 | Murakami et al. | |

FOREIGN PATENT DOCUMENTS

| | | |
|---|---|---|
| EP | 2 357 013 A1 | 8/2011 |
| EP | 2 862 588 A1 | 4/2015 |
| JP | 2002-515302 A | 5/2002 |
| JP | 2005-537116 A | 12/2005 |
| JP | 2010-510867 A | 4/2010 |
| JP | 2013-126532 A | 6/2013 |
| WO | 99/59657 A1 | 11/1999 |
| WO | 2004/024217 A1 | 3/2004 |
| WO | 2008/067314 A2 | 6/2008 |
| WO | 2010/055608 A1 | 5/2010 |
| WO | 2011/097487 A2 | 8/2011 |
| WO | 2013/073650 A1 | 5/2013 |
| WO | 2013/099123 A1 | 7/2013 |
| WO | 2013/186997 A1 | 12/2013 |

OTHER PUBLICATIONS

The Search Report from the corresponding European Patent Application No. 15743943.1 dated Jan. 2, 2017.

* cited by examiner (a)
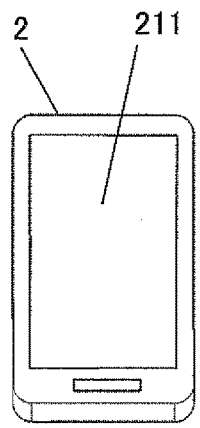
(b)
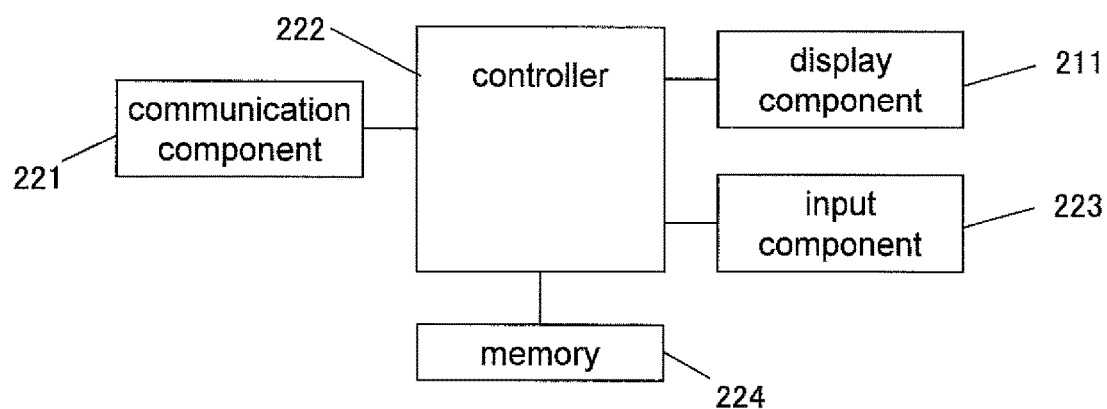
FIG. 17

PHARMACEUTICAL INJECTION DEVICE, AND PHARMACEUTICAL MANAGEMENT SYSTEM

PRIORITY

This is a National Stage Application under 35 U.S.C. §365 of International Application PCT/JP2015/051830, with an international filing date of Jan. 23, 2015, which claims priority to Japanese Patent Application No. 2014-013407 filed on Jan. 28, 2014. The entire disclosures of International Application PCT/JP2015/051830 and Japanese Patent Application No. 2014-013407 are hereby incorporated herein by reference.

TECHNICAL FIELD

Certain implementations relate to a pharmaceutical injection device that injects a pharmaceutical such as insulin or a growth hormone, for example.

BACKGROUND

A conventional pharmaceutical injection device of this type was configured so as to internally comprise a main body case having a holder for holding a pharmaceutical syringe, a drive mechanism for pushing out the pharmaceutical inside the pharmaceutical syringe through a syringe needle inside this main body case, a controller that was connected to this drive mechanism, and a display component that was connected to this controller.

The temperature inside the main body case was sensed by a temperature sensor, and when the temperature sensed by this temperature sensor rose high enough to damage the pharmaceutical in the pharmaceutical syringe, a warning was displayed on the display component.

SUMMARY

With a conventional pharmaceutical injection device, an opening on the syringe needle mounting side is provided at the front of the holder inside the main body case, so the pharmaceutical syringe inside the holder is affected by the temperature of outside air through this opening. Specifically, if there is an opening, outside air will come in on the holder side, and as a result the pharmaceutical syringe will be warmed at an early stage, which can lead to damage. For example, if the main body case is left in direct sunlight either before or after pharmaceutical injection, outside air will come in on the holder side through the opening, and will warm the pharmaceutical within a short time, which ends up damaging the pharmaceutical. Also, if the temperature sensor does not function properly, the user will be unable to find out that the pharmaceutical is in a state in which it will be damaged.

In view of this, it is an object of certain implementations to suppress damage to a pharmaceutical inside a pharmaceutical injection device.

In one aspect the pharmaceutical injection device comprises a main body case in the interior of which a pharmaceutical syringe can be mounted, a drive mechanism that is provided inside the main body case and that pushes a pharmaceutical inside the pharmaceutical syringe out of a syringe needle, a cover that opens and closes an opening on the side of the main body case on which the syringe needle is mounted, an outside air temperature sensor that measures a first temperature which is the temperature outside the main body case, a display component, and a controller that controls the drive mechanism and the display component, and acquires the first temperature at first predetermined intervals. When the cover is closed, the controller causes the display component to display information about the storage state of the pharmaceutical in the mounted pharmaceutical syringe on the basis of the first temperature.

In another aspect, the pharmaceutical injection device comprises a main body case in the interior of which a pharmaceutical syringe can be mounted, a drive mechanism that is provided inside the main body case and that pushes a pharmaceutical inside the pharmaceutical syringe out of a syringe needle, an outside air temperature sensor that measures a first temperature which is the temperature outside the main body case, an inside air temperature sensor that measures a second temperature which is the temperature inside the main body case, a display component, and a controller that controls the drive mechanism and the display component. When the first temperature is at or above a predetermined value, the controller causes the display component to display information about the storage state of the pharmaceutical in the mounted pharmaceutical syringe on the basis of the first temperature.

In yet another aspect, a pharmaceutical management system comprises the pharmaceutical injection device according to either of the above aspects, and a communication device that is connected so as to be able to communicate with the pharmaceutical injection device, and has a second controller and a second display component. The second controller acquires a temperature value measured from the pharmaceutical injection device, produces information indicating the storage state of the pharmaceutical on the basis of this temperature value, and displays this on the second display component With certain implementations, damage to the pharmaceutical inside a pharmaceutical injection device can be suppressed.

BRIEF DESCRIPTION OF THE DRAWINGS

FIG. 17 shows the simplified configuration of a portable device pertaining to Embodiment 2.

DETAILED DESCRIPTION

Certain implementations will be described through reference to the drawings.

Embodiment 1

1-1. Configuration

Figure 1:
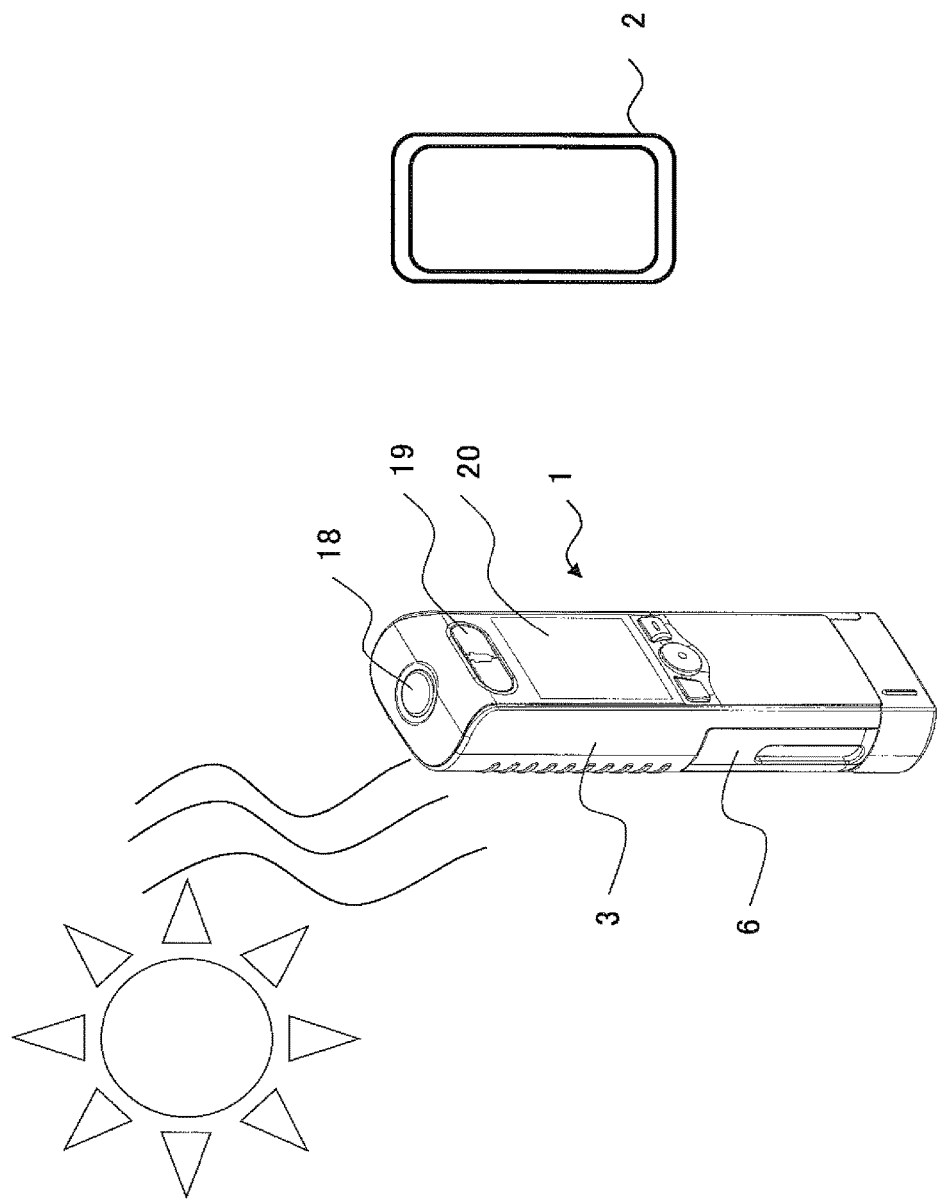
FIG. 1 is an oblique view of the pharmaceutical injection device pertaining to Embodiment 1.

In FIG. 1, 1 is a pharmaceutical injection device for injecting insulin, a growth hormone, or the like into a body (an example of a pharmaceutical injection device). The pharmaceutical injection device 1 and a portable device 2 are connected so as to be able to transmit information, as discussed below.

Figure 2:
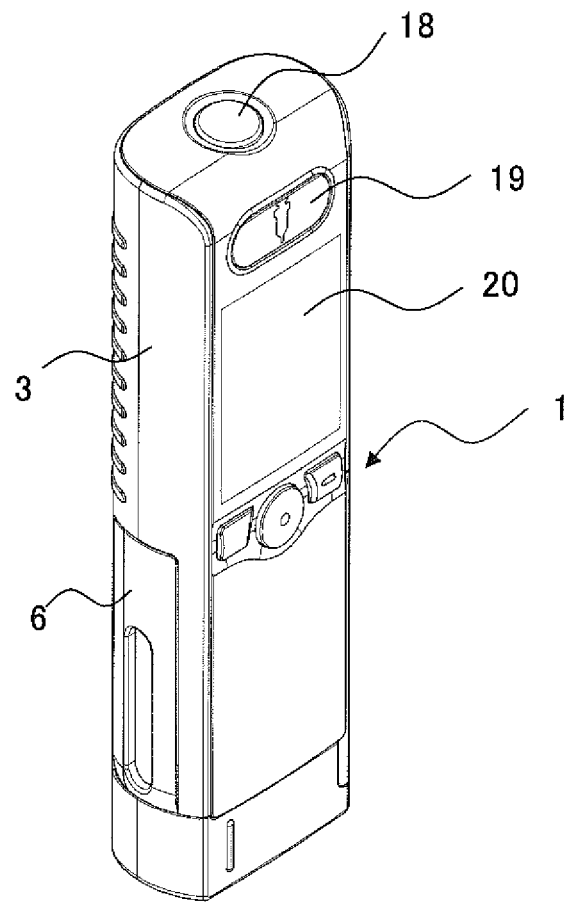
FIG. 2 is an oblique view of the same.
Figure 3:
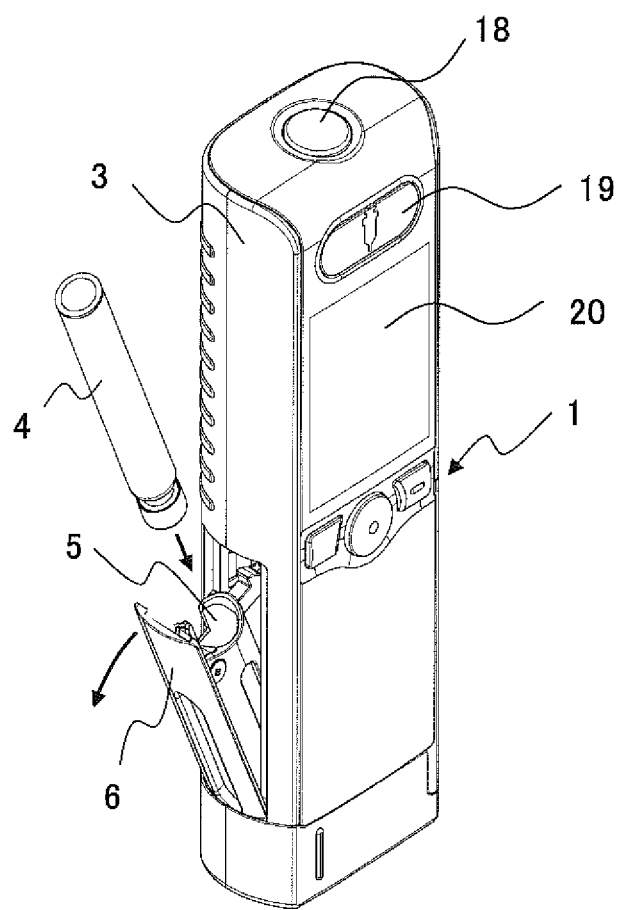
FIG. 3 is an oblique view of the same.
Figure 4:
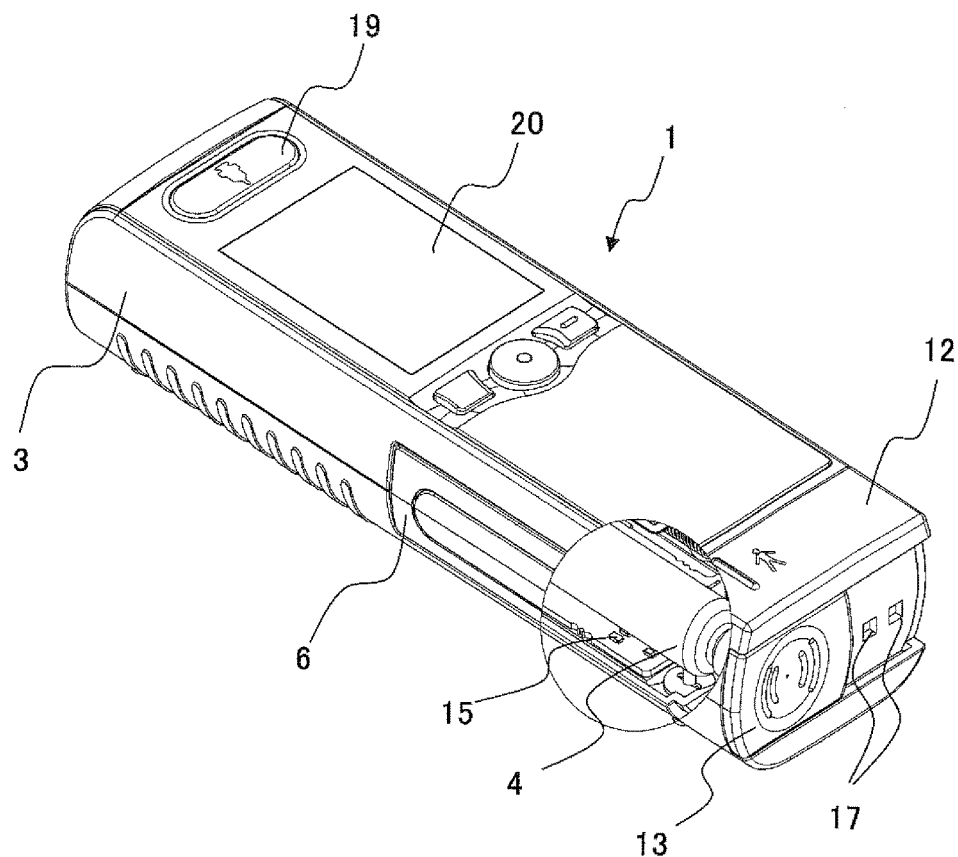
FIG. 4 is an oblique view of the same.

As shown in FIGS. 2 to 4, the pharmaceutical injection device 1 is such that a holder 5 of a pharmaceutical syringe 4 is provided inside a main body case 3 that is in the form of a box that is longer than it is wide (an example of a main body case). The pharmaceutical syringe 4 is put into the holder 5 in a state in which a lid 6 is open as in FIG. 3, and this lid 6 is closed as in FIG. 2 to create a state in which the pharmaceutical syringe 4 is housed inside the main body case 3.

Figure 5:
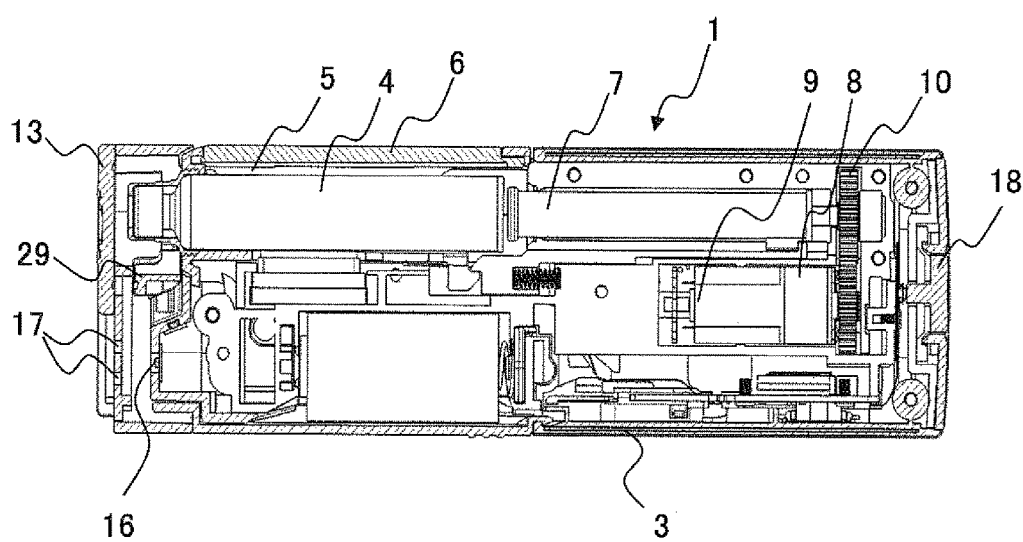
FIG. 5 is a cross section of the same.

As shown in FIG. 5, a drive means 8 (an example of a drive mechanism) for pushing a piston 7 from the rear end of the pharmaceutical syringe 4 is provided inside the main body case 3. The drive means 8 is made up of a motor 9 and a gear 10, and is configured to move the piston 7 forward when the gear 10 turns.

Figure 7:
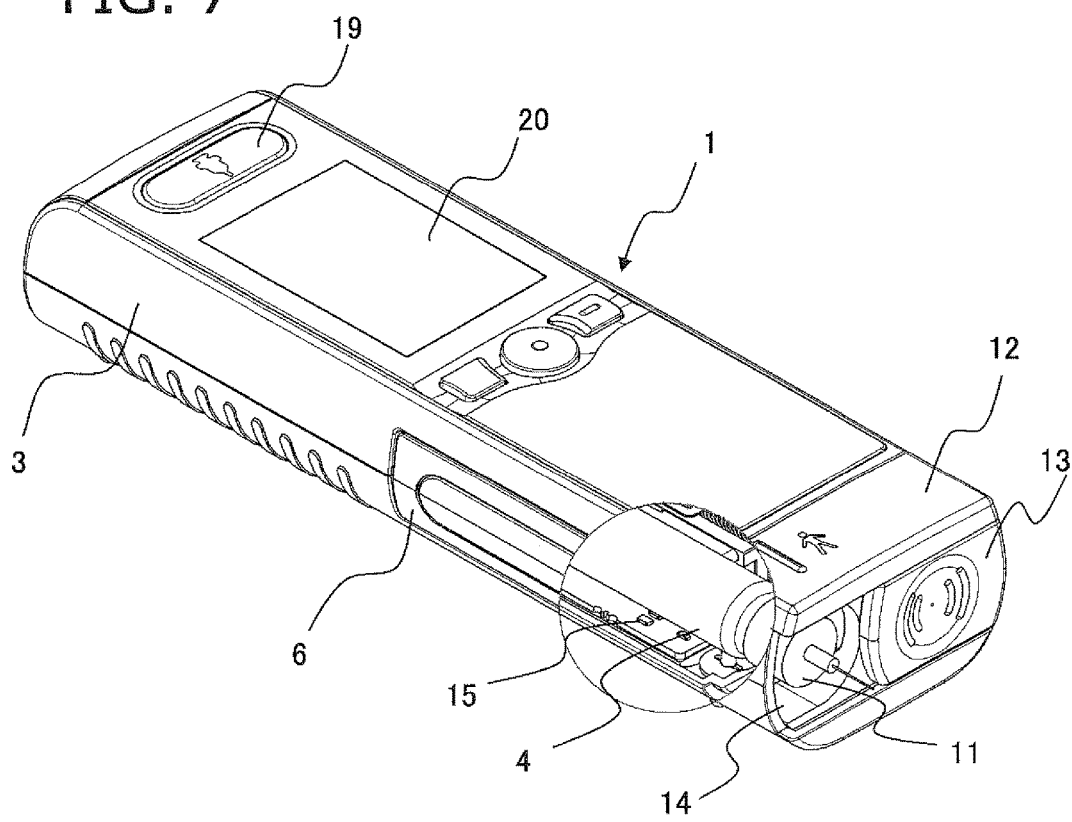
FIG. 7 is an oblique view of the same.
Figure 9:
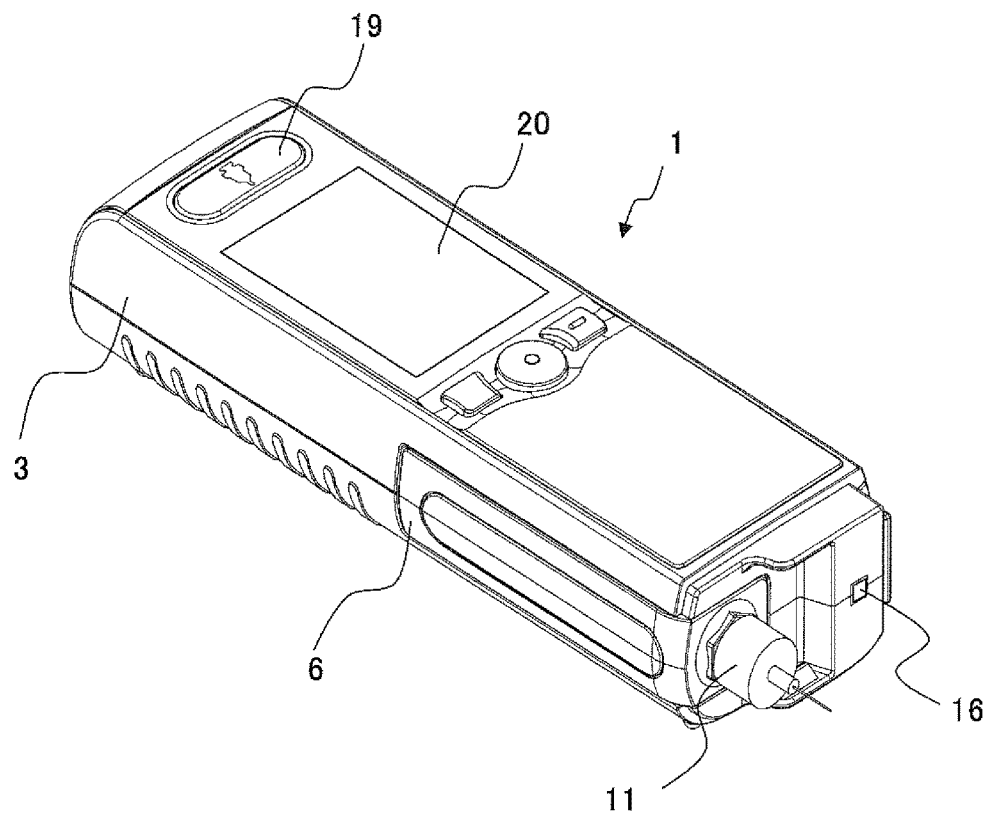
FIG. 9 is an oblique view of the same.
Figure 10:
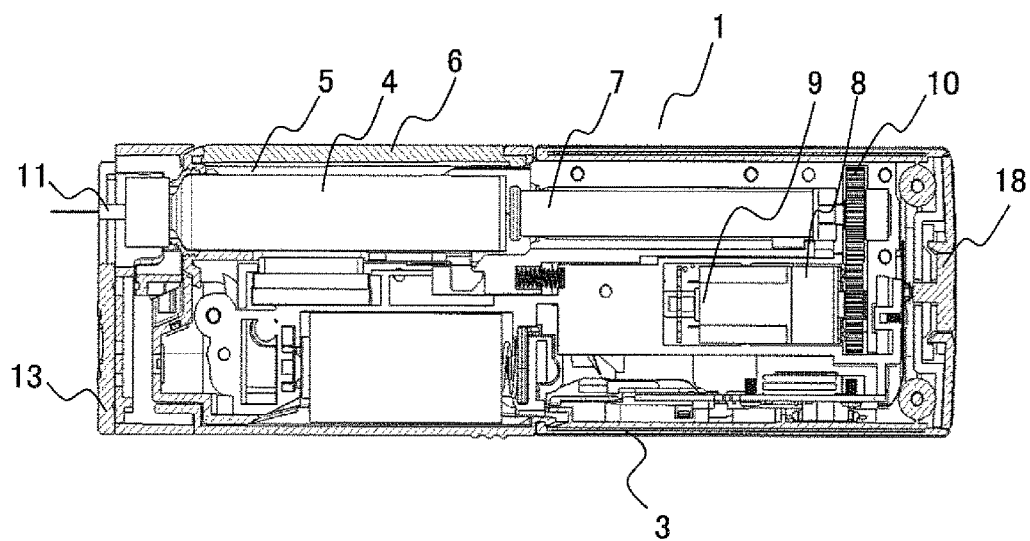
FIG. 10 is a cross section of the same.

As shown in FIGS. 7, 9, and 10, a syringe needle 11 is mounted to the front of the pharmaceutical syringe 4. If the piston 7 is moved forward in a state in which this syringe needle 11 has pierced the skin, the pharmaceutical inside the pharmaceutical syringe 4 will be injected into the body.

In this embodiment, a cap 12 is mounted to the front of the main body case 3. This cap 12 is provided with a cover 13 that openably and closeably covers the front of the holder 5 (an example of a cover).

That is, as shown in FIG. 7, this cap 12 is provided with an opening 14 at the front of the holder 5. The syringe needle 11 is mounted to the distal end side of the pharmaceutical syringe 4 in a state in which the cover 13 has been opened. In this state, the distal end of the syringe needle 11 sticks out to the front side of the opening 14, and therefore pierces the skin. After this, the piston 7 is moved forward and the pharmaceutical is injected into the body as discussed above.

After this pharmaceutical injection, or before the pharmaceutical injection before the syringe needle 11 is mounted, the opening 14 is covered by the cover 13 in a state in which the syringe needle 11 has not been mounted to the front of the pharmaceutical syringe 4, as shown in FIG. 4.

As shown in FIG. 4, in this embodiment, the pharmaceutical is stored until the next pharmaceutical injection in a state in which the pharmaceutical syringe 4 has been mounted, inside the holder 5 of the main body case 3.

As shown in FIG. 1, it is recommended that this storage of the pharmaceutical is carried out away from direct sunlight. That is, as shown in FIG. 1, when direct sunlight hits the main body case 3, the temperature inside the holder 5 of the main body case 3 rises, and this also raises the temperature of the pharmaceutical syringe 4. As a result, the pharmaceutical inside the pharmaceutical syringe 4 can be damaged.

Figure 6:
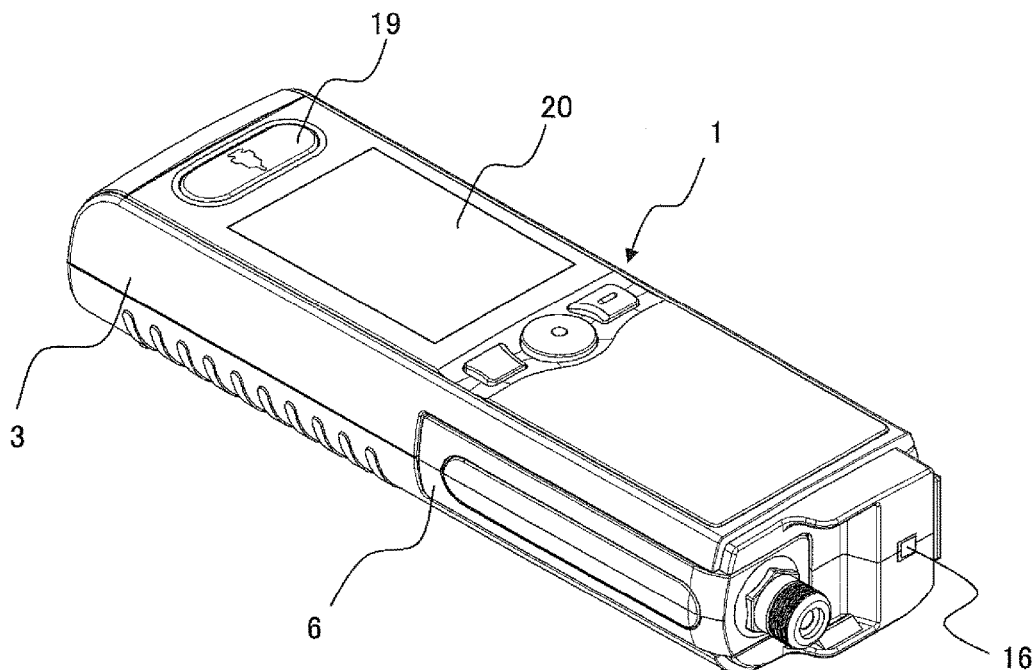
FIG. 6 is an oblique view of the same.

Therefore, the pharmaceutical injection device 1 is usually kept indoors in a place where it will not be affected by heating devices or the like, but if it should happen to be kept in an unsuitable place (where its temperature will rise), a warning about storage is issued. More specifically, the pharmaceutical injection device 1 is provided with an inside air temperature sensor 15 that senses the temperature of the holder 5 of the main body case 3 as shown in FIGS. 4 and 7, and with an outside air temperature sensor 16 that senses the temperature outside the main body case 3 as shown in FIG. 6 (an example of an outside air temperature sensor).

As shown in FIG. 4, a plurality of outside air measurement openings 17 are provided to the portion of the cap 12 corresponding to the outside air temperature sensor 16.

As shown in FIG. 4, these outside air measurement openings 17 are open, and not covered by the cover 13, even when the opening 14 is covered by the cover 13. Outside air moves into the cap 12 (the inside of the main body case 3) through these outside air measurement openings 17. This allows the temperature of outside air to be sensed by the outside air temperature sensor 16.

As shown in FIGS. 4 and 5, in a state in which the opening 14 has been covered with the cover 13, and the outside air temperature is sensed by the outside air temperature sensor 16, the space of the holder 5 and the space in which the outside air temperature sensor 16 is provided is divided up by a partition wall 29 in the main body case 3. That is, the partition wall 29 is provided in order to keep outside air from coming in on the holder 5 side in a state in which the opening 14 is covered by the cover 13.

A power switch 18, an inject switch 19, and a display component 20 (an example of a display component) are provided on the surface of the main body case 3.

Figure 8:
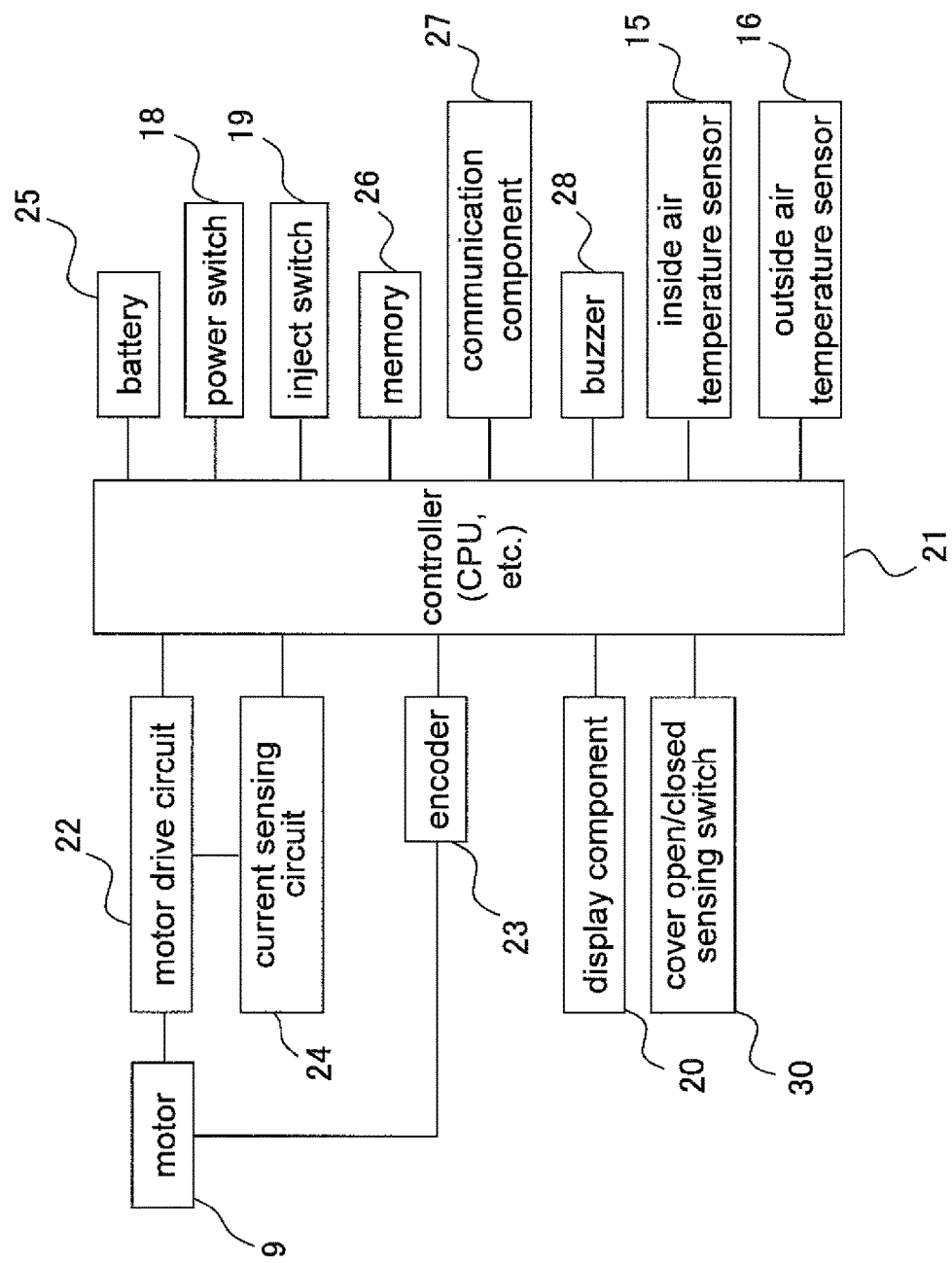
FIG. 8 control block diagram of the same.

FIG. 8 shows the control blocks of the pharmaceutical injection device 1, in which the inside air temperature sensor 15, the outside air temperature sensor 16, the power switch 18, the inject switch 19, and the display component 20 are connected to a controller 21 (an example of a controller). The motor 9 is connected to the controller 21 via a motor drive circuit 22 and an encoder 23. The motor drive circuit 22 is connected to the controller 21 via a current sensing circuit 24. The controller 21 is connected to a cover open/closed sensing switch 30 that senses whether the opening 14 is not covered by the cover 13 (that is, is open) as shown in FIG. 7, the opening 14 is covered by the cover 13 as shown in FIG. 4 (that is, is closed). The controller 21 is also connected to a battery 25, a memory 26 that records data and programs, a communication component 27 that sends a warning to the portable device 2 shown in FIG. 1, and a buzzer 28 for issuing a warning.

The controller 21 includes a CPU or another such processor. The controller 21 reads a specific computer program for executing a pharmaceutical storage operation (discussed below) or the operation of the pharmaceutical injection device 1, from the memory and executes this program.

Figure 11:
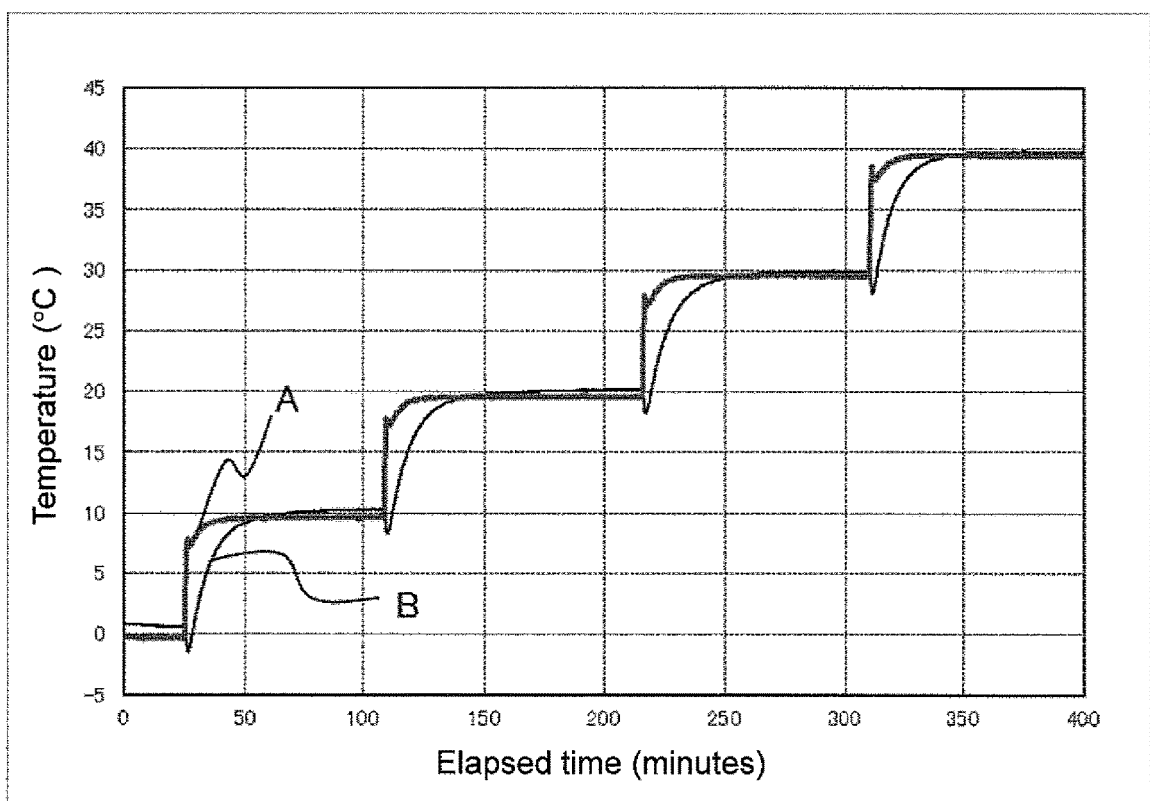
FIG. 11 is a graph of the temperature change versus elapsed time in this pharmaceutical injection device.

The A line in FIG. 11 indicates the temperature measured by the outside air temperature sensor 16 when the pharmaceutical injection device 1 is stored in a state in which the opening 14 has been covered with the cover 13 as shown in FIGS. 4 and 5.

In contrast, the B line indicates the temperature measured by the inside air temperature sensor 15 when the pharmaceutical injection device 1 is stored in a state in which the opening 14 has been covered with the cover 13 as shown in FIGS. 4 and 5.

As will be understood from FIG. 11, when the pharmaceutical injection device 1 is being stored in a state in which the opening 14 provided at the front of the holder 5 holding the pharmaceutical syringe 4 is covered with the cover 13, the rise in the temperature of the holder 5 is more gradual than when the device is stored in a state in which the opening 14 is not covered with the cover 13. In this example, we shall assume that there are no members that serve as a heat source, such as a rechargeable battery, inside the device.

This embodiment focuses on this point, and a feature thereof is that the pharmaceutical in the pharmaceutical syringe 4 can be properly stored. That is, that the pharmaceutical of the pharmaceutical syringe 4 in the holder 5 will be damaged is predicted by measuring the outside air temperature with the outside air temperature sensor 16, and a warning is issued before the pharmaceutical is actually damaged. The result of doing this is that a warning is issued in a state in which the outer peripheral portion of the pharmaceutical syringe 4 has not reached the temperature at which the pharmaceutical will be damaged, as shown by the B line in FIG. 11, so damage to the pharmaceutical can be suppressed.

1-2. Operation 1-2-1. Pharmaceutical Injection Operation

With the above configuration, when the pharmaceutical is injected into the body, the cover 13 of the main body case 3 stored in the state of FIG. 4 is slid over as shown in FIG. 7. Then, the syringe needle 11 is mounted to the pharmaceutical syringe 4 as shown in FIG. 7, and the power switch 18 is pressed.

The syringe needle 11 then pierces the skin in this state. If the user presses the inject switch 19 in this state, the motor 9 is driven, and as a result the piston 7 is pushed forward by the gear 10. This causes the pharmaceutical in the pharmaceutical syringe 4 to be injected through the syringe needle 11 into the body.

1-2-2. Pharmaceutical Storage Operation

As shown in FIGS. 4 and 5, after the pharmaceutical injection discussed above, the syringe needle 11 is removed from the pharmaceutical syringe 4. The cover 13 is then slid over to cover the opening 14.

The fact that the opening 14 has been covered with the cover 13 at this point is detected by the cover open/closed sensing switch 30, and a pharmaceutical storage operation is executed in this state.

A pharmaceutical storage operation includes a state in which the temperature of the holder 5 is measured by the inside air temperature sensor 15, and a state in which the outside air temperature is measured by the outside air temperature sensor 16. Of these, the measurement of the temperature of the holder 5 by the inside air temperature sensor 15 is always performed, regardless of whether the power switch 18 is on or off, so the user is warned, urged to take caution, or otherwise informed about the storage state, as will be discussed below.

In contrast, the measurement of the outside air temperature by the outside air temperature sensor 16 is executed in a state in which the opening 14 has been covered by the cover 13 as shown in FIG. 4.

Temperature Sensing by Inside Air Temperature Sensor 15

First, the temperature sensing done by the inside air temperature sensor 15 will be described through reference to FIGS. 12 and 13.

Figure 12:
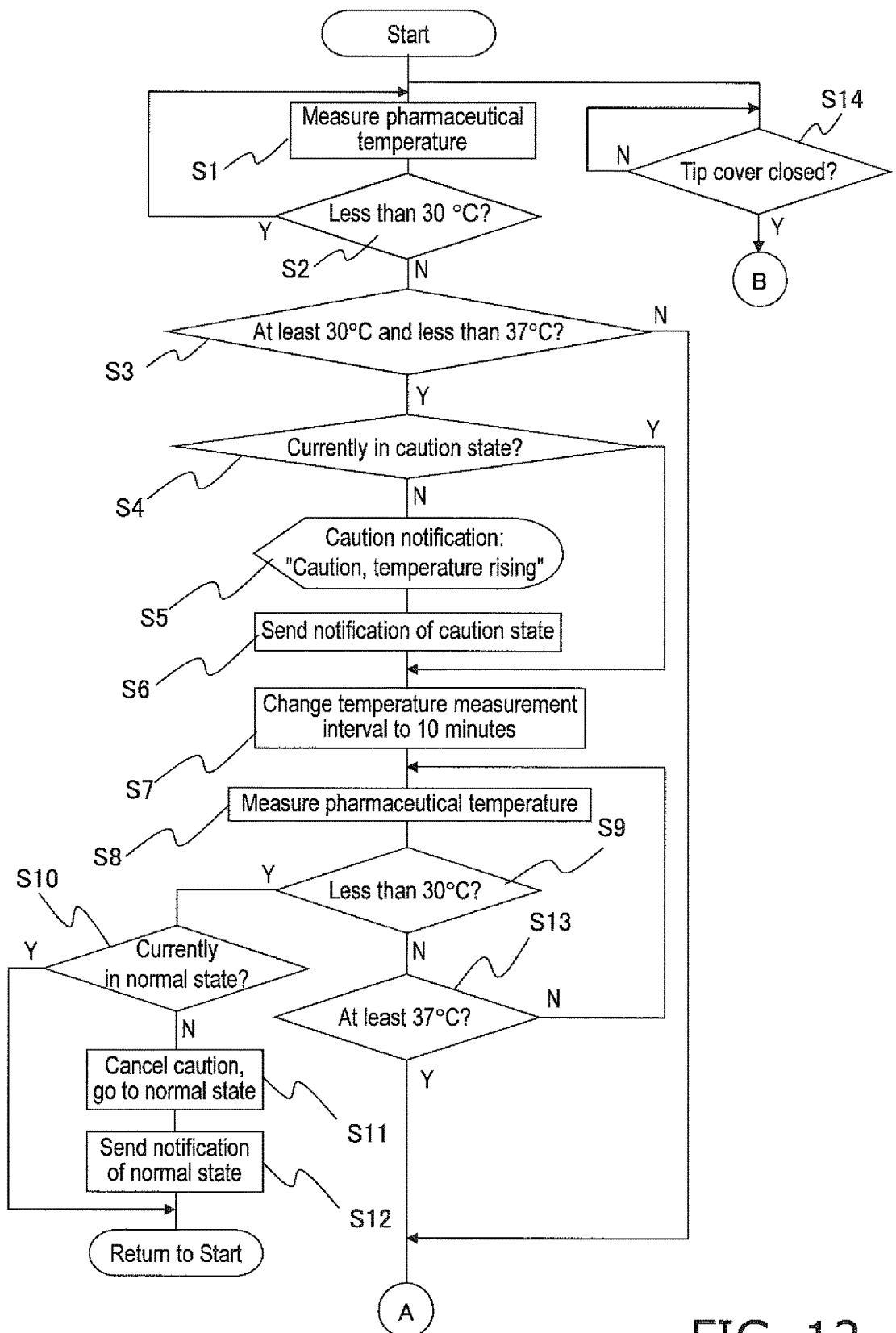
FIG. 12 is an operational flowchart of the same.

The temperature measurement done by the inside air temperature sensor 15 is executed at specific, preset intervals (such as every 60 minutes) (S1 in FIG. 12).

The controller 21 determines whether or not the temperature sensed by the inside air temperature sensor 15 is at or above 30° C. (S2 in FIG. 12). If the temperature is at or above 30° C., the controller 21 then determines whether or not this temperature is within a range of from 30° C. to less than 37° C. (S3 in FIG. 12).

Figure 16:
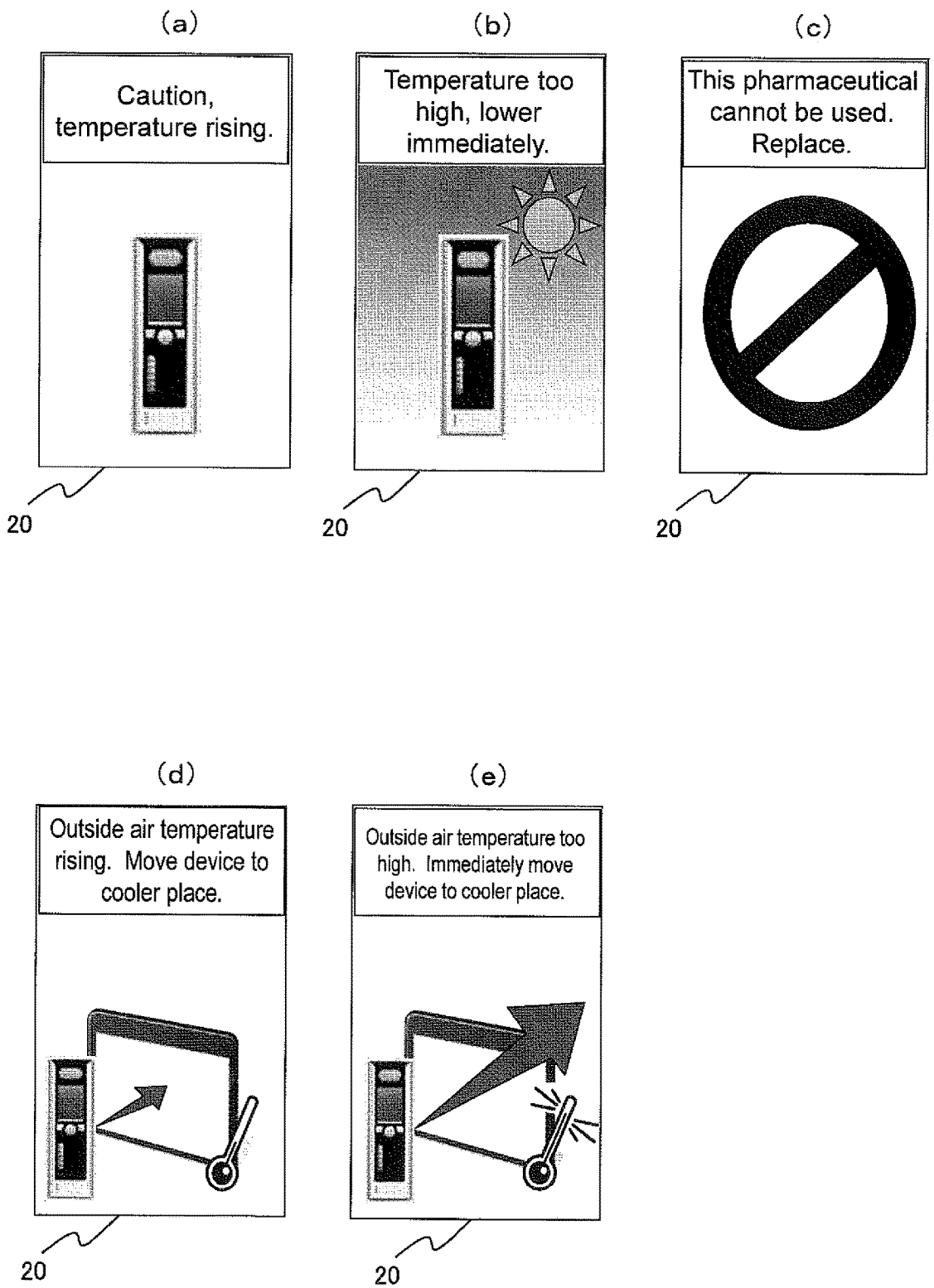
FIG. 16 consists of diagrams showing the display component of the same.

The controller 21 determines whether the pharmaceutical injection device 1 is currently in a caution state if the temperature is within a range of from 30° C. to less than 37° C. (S4 in FIG. 12). If the device is not currently in a caution state, information that urges caution, such as the "Caution, temperature rising" shown in FIG. 16a, is displayed on the display component 20 in order to warn the user (S5 in FIG. 12).

The controller 21 also sends a notification of "Caution, temperature rising" or the like from the communication component 27 to the portable device 2 (S6 in FIG. 12).

The controller 21 then changes (shortens) the temperature measurement interval by the inside air temperature sensor 15 to 10 minutes (S7 in FIG. 12), after which the temperature is measured at this measurement interval (S8 in FIG. 12).

Next, the controller 21 determines whether the measured temperature is lower than 30° C. (S9 in FIG. 12), and if it is, the controller 21 determines whether the pharmaceutical injection device 1 was in a normal state up to now (S10 in FIG. 12).

In this case, since the pharmaceutical injection device 1 is in a state in which caution was urged in S5 above, the controller 21 determines that the device was not in a normal state up to now, and deletes the caution display from the display component 20 (S11 in FIG. 12). The controller 21 also sends a notification from the communication component 27 to the portable device 2 to the effect that a normal state has been achieved (S12 in FIG. 12).

That is, upon receiving the caution in S5 above, the user of the pharmaceutical injection device 1 moves the pharmaceutical injection device 1 from a situation in which its temperature was being raised by exposure to direct sunlight, etc. as shown in FIG. 1, for example, into the shade. As a result, the temperature sensed by the inside air temperature sensor 15 can be lowered.

Also, if it was determined in S9 above that the temperature was at or over 30° C., the controller 21 determines whether or not this temperature is at or over 37° C. (S13 in FIG. 12). If the temperature is at or over 37° C., the controller 21 determines whether or not the pharmaceutical injection device 1 is currently in a warning state, which is more urgent than a caution state (S1 in FIG. 13).

Figure 13:
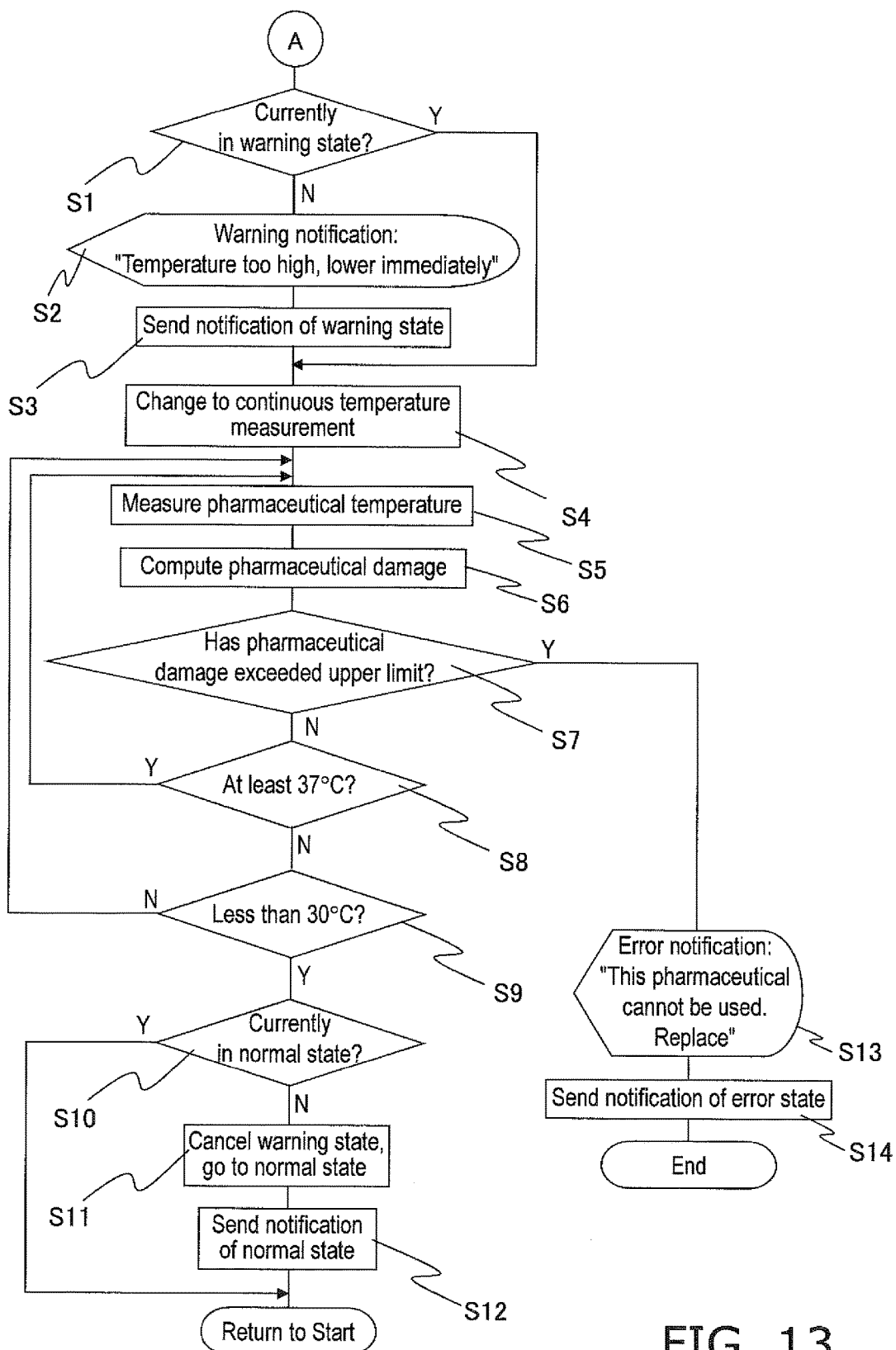
FIG. 13 is an operational flowchart of the same.

At this point the pharmaceutical injection device 1 is still in a caution state, so if the temperature is at or over 37° C., the controller 21 causes the display component 20 to display a warning display such as "Temperature too high, lower immediately" as shown in FIG. 16b (S2 in FIG. 13). The controller 21 also sends a warning notification from the communication component 27 to the portable device 2 (S3 in FIG. 13).

Once the pharmaceutical injection device 1 enters this warning state, the controller 21 changes the temperature measurement done by the inside air temperature sensor 15 to a continuous measurement mode (S4 in FIG. 13), and executes temperature measurement in this state (S5 in FIG. 13).

Next, the controller 21 adds up the time during which the device has been at or over the warning temperature (such as 37° C.) (S6 in FIG. 13). The controller 21 determines whether or not this sum has exceeded a specific value (pharmaceutical damage upper limit value) (S7 in FIG. 13).

If this sum has not exceeded the specific value, the controller 21 then determines whether or not the temperature measured by the inside air temperature sensor 15 is at or over 37° C. (S8 in FIG. 13).

If the temperature is at or over 37° C., the controller 21 goes back to S5 in FIG. 13. If the temperature is under 37° C., the controller 21 determines whether or not the temperature measured by the inside air temperature sensor 15 is lower than 30° C. (S9 in FIG. 13).

Here, if the temperature is at or over 30° C., the controller 21 goes back to S5 in FIG. 13. If the temperature is under 30° C., the controller 21 determines whether or not the pharmaceutical injection device 1 is currently in a normal state (S10 in FIG. 13).

At this point, as mentioned above, the pharmaceutical injection device 1 is in a state in which a warning has been issued, so it is not in a normal state. Therefore, the controller 21 cancels the warning display on the display component 20 (S11 in FIG. 13). The controller 21 also notifies the portable device 2, via the communication component 27, that a normal state has been achieved (S12 in FIG. 13).

That is, upon receiving the warning notification in S2 of FIG. 13, the user of the pharmaceutical injection device 1 moves the pharmaceutical injection device 1 from a situation in which its temperature was being raised by exposure to direct sunlight, etc. as shown in FIG. 1, for example, into the shade. As a result, the temperature sensed by the inside air temperature sensor 15 can be lowered.

In contrast, if the value added up in S7 in FIG. 13 has exceeded the pharmaceutical damage upper limit value, the controller 21 causes the display component 20 to give an error display such as "This pharmaceutical cannot be used. Replace." as shown in FIG. 16c (S13 in FIG. 13). The controller 21 also notifies the portable device 2, via the communication component 27, that the device has entered an error state (S14 in FIG. 13).

Here, the controller 21 may put the pharmaceutical injection device 1 in a state in which its use is prohibited. Putting the pharmaceutical injection device 1 in a prohibited use state here means that the operation of the pharmaceutical injection device 1 is prohibited by the controller 21 by stopping operation of the motor drive circuit 22, or deactivating the inject switch 19, for example. This prohibited use state of the pharmaceutical injection device 1 may be cancelled when the mounting of a new pharmaceutical syringe 4 is detected, for example.

Temperature Sensing by Outside Air Temperature Sensor 16

Next, the temperature sensing done by the outside air temperature sensor 16 will be described through reference to FIGS. 14 and 15.

In the above-mentioned FIG. 12, at the start of the flow, the controller 21 determines whether or not the opening 14 has been covered by the cover 13 (S14 in FIG. 12). If a closed state is detected in which the cover 13 is covering the opening 14 as in FIG. 4, the operation moves to measurement of the outside air temperature by the outside air temperature sensor 16 as shown in FIGS. 14 and 15.

Figure 14:
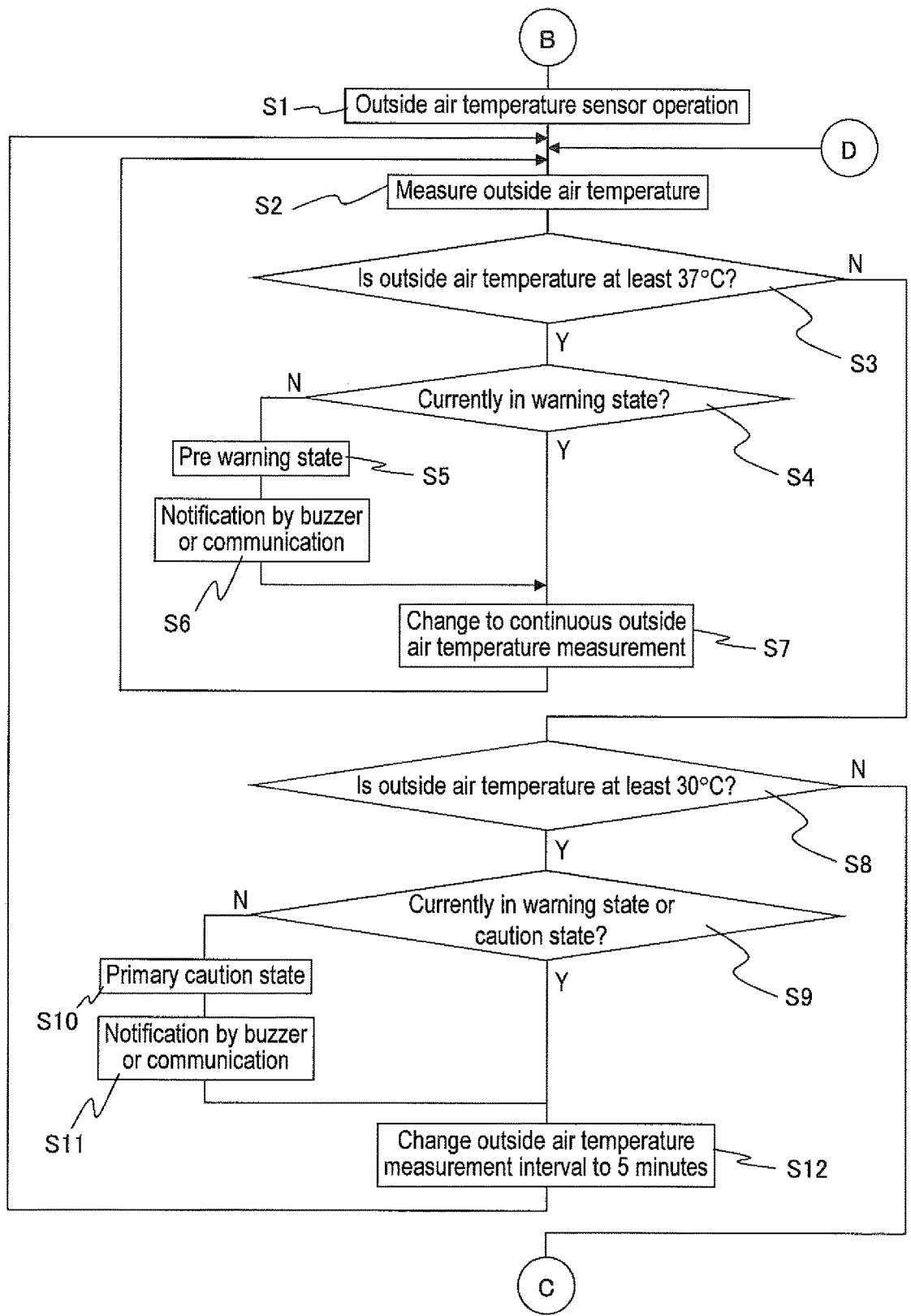
FIG. 14 is an operational flowchart of the same.

First, the controller 21 operates the outside air temperature sensor 16 (S1 in FIG. 14). This temperature measurement by the outside air temperature sensor 16 is executed at specific, preset intervals (such as every 60 minutes) (S2 in FIG. 14).

Next, the controller 21 determines whether or not the temperature sensed by the outside air temperature sensor 16 is at or over 37° C. (S3 in FIG. 14).

If the temperature measured by the outside air temperature sensor 16 is at or over 37° C., the controller 21 confirms whether or not the current state of the pharmaceutical injection device 1 is a warning state (S4 in FIG. 14).

If the current state is not a warning state, the controller 21 sets a "pre-warning state," and causes the display component 20 to display a pre-warning message such as "Outside air temperature too high. Immediately move device to cooler place" as shown in FIG. 16e (S5 in FIG. 14). The controller 21 also gives a notification by the buzzer 28, and uses the communication component 27 to notify the portable device 2 of this pre-warning (S6 in FIG. 14).

After this, the controller 21 changes the measurement of the outside air temperature to a continuous measurement mode (S7 in FIG. 14). The controller 21 also moves to the processing in S7 in FIG. 14 and changes the measurement of the outside air temperature to a continuous measurement mode if the current state of the pharmaceutical injection device 1 is a warning state in S4 in FIG. 14.

After this, the controller 21 goes back to S2 in FIG. 14, the outside air temperature is measured by the outside air temperature sensor 16, and the above-mentioned steps S2 to S7 in FIG. 14 are repeated.

On the other hand, in S3 in FIG. 14, if the outside air temperature measured by the outside air temperature sensor 16 has dropped under 37° C., the controller 21 determines whether or not the measured outside air temperature is at or over 30° C. (S8 in FIG. 14).

If the outside air temperature is at or over 30° C., the controller 21 determines whether the current state of the pharmaceutical injection device 1 is a warning state or a caution state (S9 in FIG. 14). If the pharmaceutical injection device 1 is in neither of these states, the controller 21 sets the current state to "primary caution state," and causes the display component 20 to give a primary caution display such as "Outside air temperature rising. Move device to cooler place" as shown in FIG. 16d (S10 in FIG. 14). The controller 21 then performs notification with the buzzer 28, and sends a primary caution notification through the communication component 27 to the portable device 2 (S11 in FIG. 14).

Next, the controller 21 changes (shortens) the outside air temperature measurement interval to 5 minutes (S12 in FIG. 14). After this, controller 21 goes back to S2 in FIG. 14, and the outside air temperature is measured by the outside air temperature sensor 16. From there on the controller 21 repeats steps S2 to S12 in FIG. 14.

The controller 21 also moves to the processing in S12 in FIG. 14, changes the outside air temperature measurement interval, and goes back to S2 in FIG. 14 if the current state of the pharmaceutical injection device 1 is a warning state or a caution state in S9 in FIG. 14.

Figure 15:
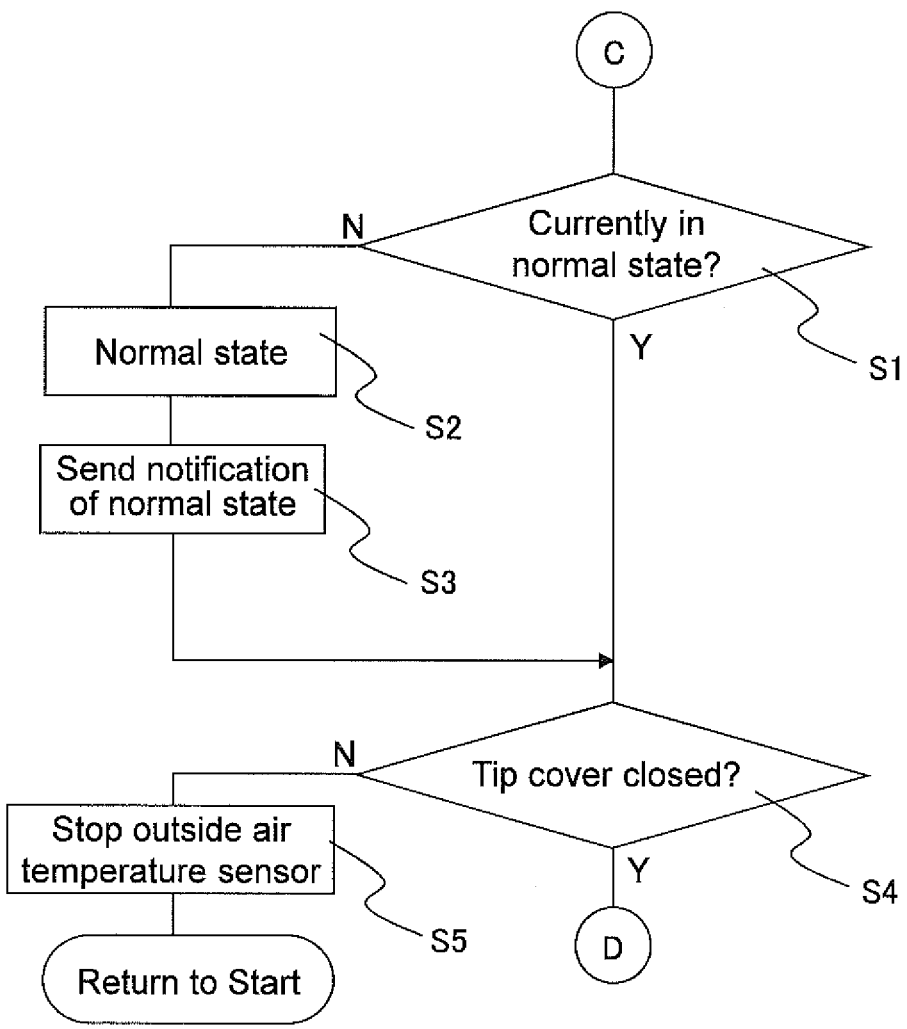
FIG. 15 is an operational flowchart of the same.

On the other hand, if the measurement temperature by the outside air temperature sensor 16 has dropped under 30° C. in S8 in FIG. 14, the controller 21 moves to the processing S1 in FIG. 15.

The controller 21 then determines whether or not the current state of the pharmaceutical injection device 1 is a normal state (S1 in FIG. 15).

Here, if the current state of the pharmaceutical injection device 1 is not a normal state, the controller 21 sets the current state to "normal state," cancels the caution display, warning display, etc., and causes the display component 20 to display a normal state (S2 in FIG. 15). The controller 21 also notifies the portable device 2, etc., via the communication component 27, that the state is now normal (S3 in FIG. 15).

After this, the controller 21 uses the cover open/closed sensing switch 30 to detect whether or not the cover 13 is closed (S4 in FIG. 15). Also, if the current state of the pharmaceutical injection device 1 is a normal state in S1 in FIG. 15, the controller 21 moves to the processing of S4 in FIG. 15, and detection of whether the cover 13 is open or closed is performed.

At this point, if the cover open/closed sensing switch 30 finds that the cover 13 is not closed (that is, that it is open), the controller 21 stops the outside air temperature sensor 16 (S5 in FIG. 15) and goes back to Start in FIG. 12. On the other hand, if the cover 13 is closed in S4 in FIG. 15, the controller 21 goes back to the processing of S2 in FIG. 14.

1-3. Features

As discussed above, the pharmaceutical injection device 1 pertaining to this embodiment (an example of a pharmaceutical injection device) comprises the main body case 3 in whose interior the pharmaceutical syringe 4 can be mounted (an example of a main body case), the drive means 8 that is provided inside the main body case 3 and pushes the pharmaceutical inside the pharmaceutical syringe 4 out of a syringe needle 11 (an example of a drive mechanism), the cover 13 that opens and closes the opening 14 on the side of the main body case 3 on which the syringe needle is mounted (an example of a cover), the outside air temperature sensor 16 that measures a first temperature, which is the temperature outside the main body case 3 (an example of an outside air temperature sensor), the display component 20 (an example of a display component), and the controller 21 that controls the drive means 8 and the display component 20 and acquires the first temperature at specific intervals (an example of a controller). When the cover is closed, the controller 21 causes the display component 20 to display information about the storage state of the pharmaceutical in the mounted pharmaceutical syringe on the basis of the first temperature. This allows damage to the pharmaceutical in the pharmaceutical injection device 1 to be suppressed.

Specifically, when the cover 13 is closed, the outside air temperature outside the main body case 3 is measured by the outside air temperature sensor 16, and information about the storage state of the pharmaceutical is displayed on the display component 20 according to this temperature measured by the outside air temperature sensor 16. The user can find out beforehand what the storage state of the pharmaceutical is corresponding to the outside air temperature, which is affected by the ambient temperature sooner than the temperature in the interior of the main body case 3 (inside air temperature). Therefore, if there is the risk that the temperature of the pharmaceutical syringe 4 in the main body case 3 will rise, the user can change the storage location before this happens, for example, thereby preventing damage to the pharmaceutical. As a result, damage to the pharmaceutical in the pharmaceutical injection device 1 can be suppressed.

The user can also properly grasp the storage state of the pharmaceutical by checking the message sent to the portable device 2, and as a result can prevent damage to the pharmaceutical in the pharmaceutical injection device 1.

Embodiment 2

In Embodiment 2, a pharmaceutical management operation using the portable device 2 is performed by utilizing temperature data (measured values) measured and stored by the inside air temperature sensor 15 and/or the outside air temperature sensor 16 of the pharmaceutical injection device 1 to calculate the state of the pharmaceutical stored in the pharmaceutical injection device 1 or the amount of damage thereto, and to output the result.

The same symbols and/or diagrams are referred to for those components and functions that are the same as in Embodiment 1, and these will not be described again in detail.

The pharmaceutical management operation executed by the portable device 2 will now be described through reference to FIGS. 17 to 23.

2-1. Configuration

The portable device 2 is a smart phone or other such portable terminal device. As shown in FIG. 17*a*, the portable device 2 has a display component 211 provided over substantially the whole surface of a main body case with a rectangular shape, and is configured to allow touch input.

As shown in FIG. 17*b*, the portable device 2 has the display component 211 (an example of a second display component), a communication component 221, an input component 223, a memory 224, a controller 222 that is connected to the various components (an example of a second controller), and so forth. The communication component 221, the input component 223, the memory 224, and the controller 222 are provided inside the main body case. The display component 211 has a liquid crystal display, an organic EL display, or the like, and displays a screen 100 that goes along with the pharmaceutical management operation, as discussed below. The communication component 221 is connected to the pharmaceutical injection device 1 and sends and receives data and control signals to and from the pharmaceutical injection device 1. The input component 223 is constituted by control buttons, a touch panel that is displayed on the display component 211, or the like. The memory 224 stores programs for executing the pharmaceutical management operation, data acquired from a specific pharmaceutical injection device 1, computation results processed by the controller 222, and so forth.

The controller 222 includes a CPU or other such processor. The controller 21 reads from memory a specific computer program for executing the pharmaceutical management operation (discussed below), and executes and processes this program.

With the above configuration, the portable device 2 that executes the pharmaceutical management operation may be a personal computer.

2-2. Operation 2-2-1. Output of Pharmaceutical Storage State

The operation for using the temperature data measured by the pharmaceutical injection device 1 to analyze the storage state of the pharmaceutical in the pharmaceutical injection device 1 and to display the computation results thereof will now be described, mainly through reference to FIGS. 18 to 20.

Figure 19:
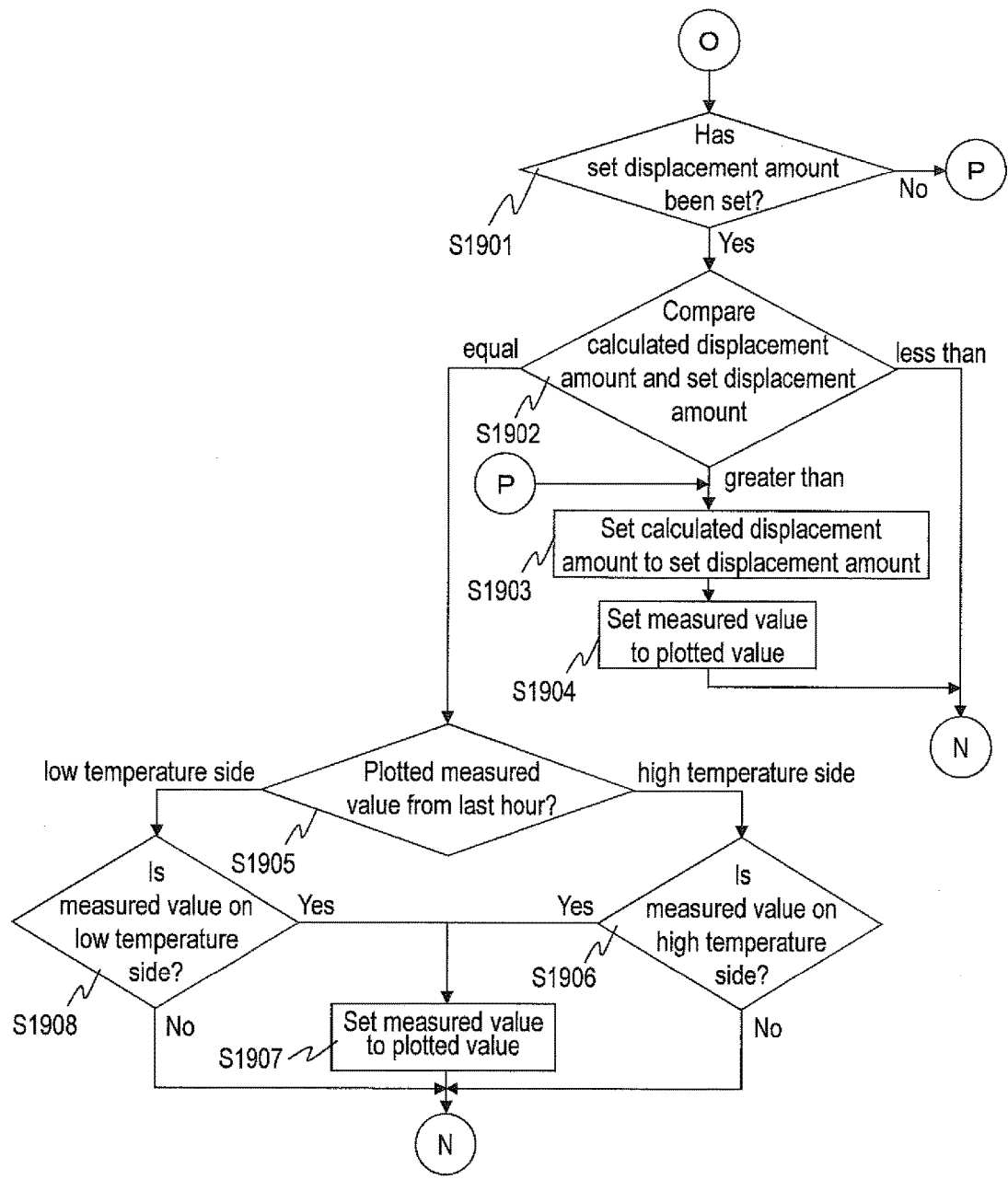
FIG. 19 is an operational flowchart of this portable device.
Figure 20:
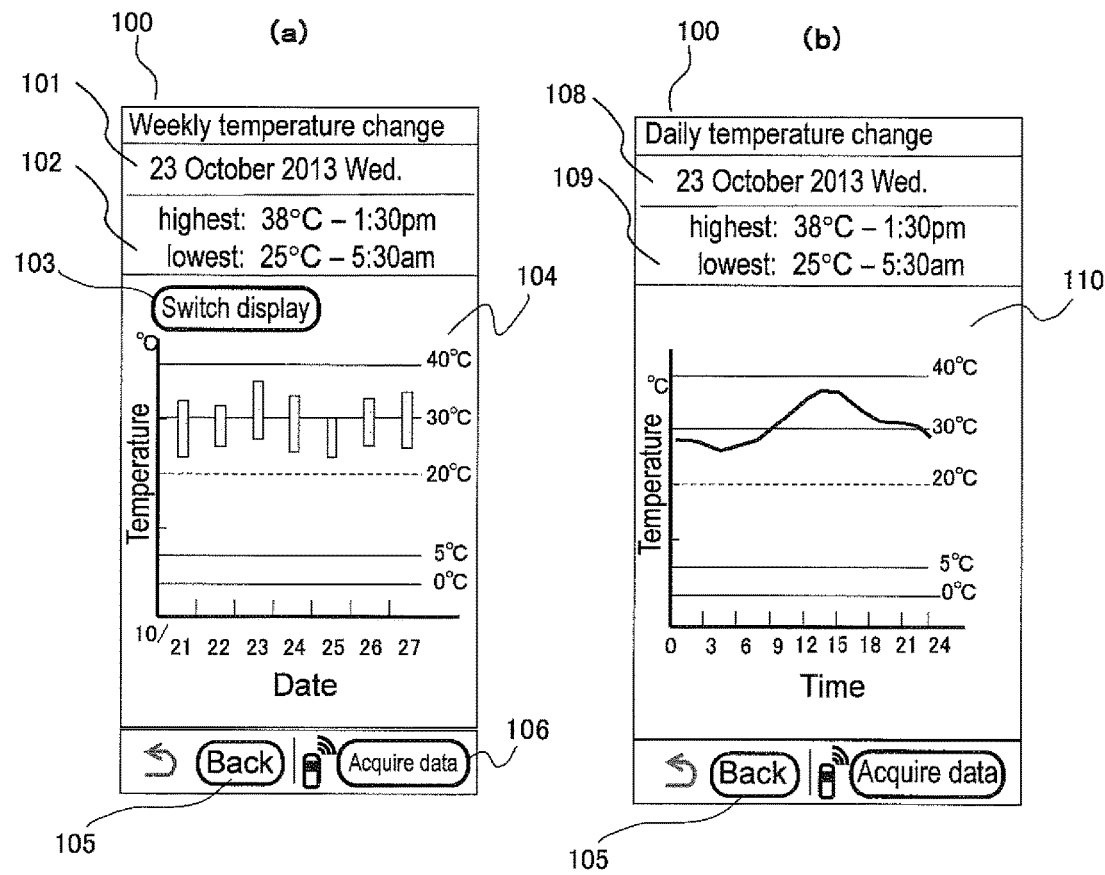
FIG. 20 shows examples of the display screen of this portable device.

First, the controller 222 of the portable device 2 runs a specific program and processes pharmaceutical storage state display (FIGS. 18 and 19), and performs the display in FIG. 20. The user touches the "data acquisition" key 106 shown in FIG. 20, and as a result the controller 222 acquires temperature data (measured values) from the pharmaceutical injection device 1 via the communication component 221, and stores this data in the memory 224. The temperature data is acquired and stored along with the measured values measured by the inside air temperature sensor 15 and/or the outside air temperature sensor 16 of the pharmaceutical injection device 1, and data indicating the date and time of measurement.

Figure 18:
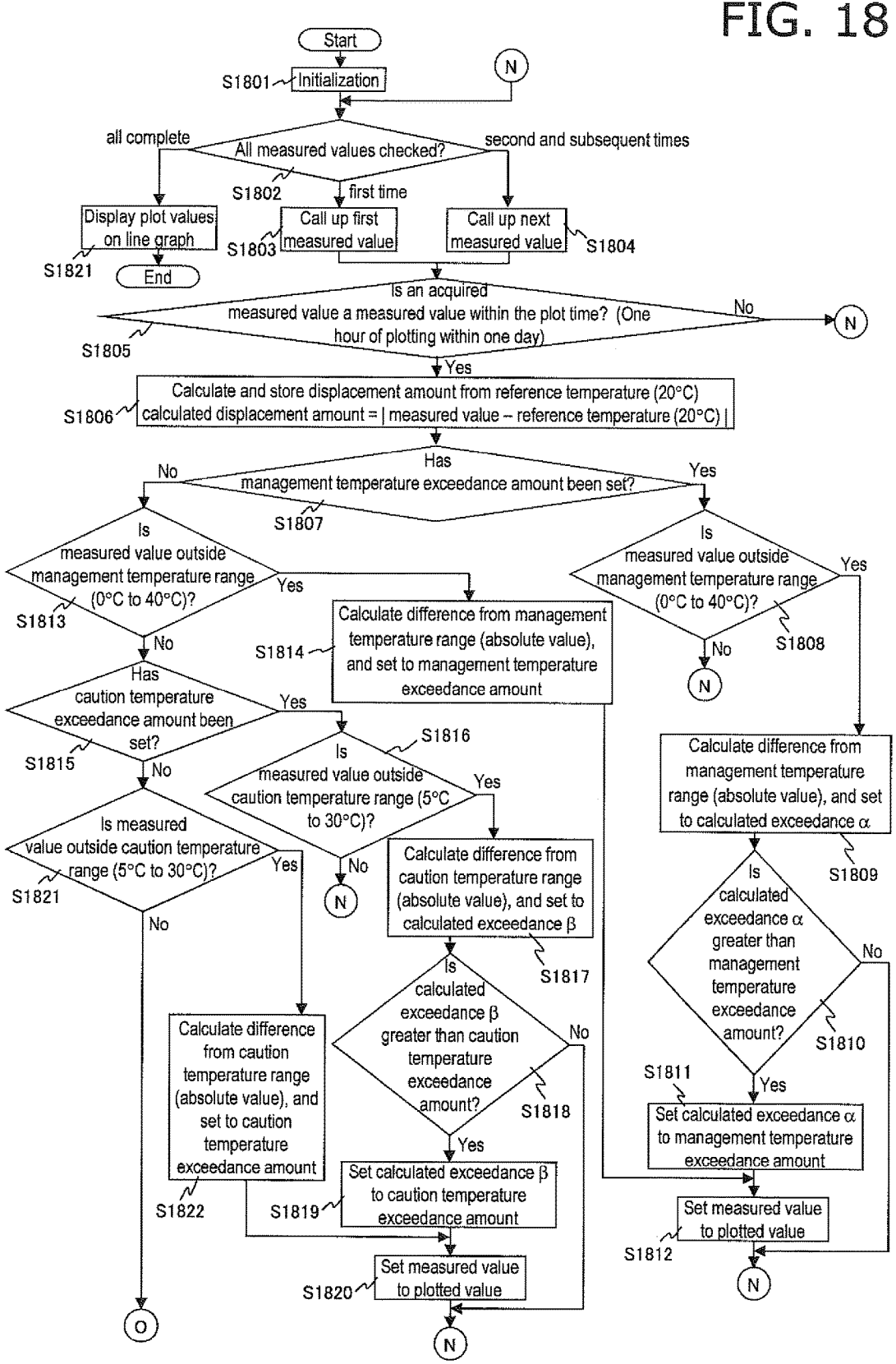
FIG. 18 is an operational flowchart of this portable device.

Next, the controller 222 performs the operation in FIG. 18 to analyze all of the acquired data into temperature data by date and time, and to store plot values in the memory 224 for each plot interval of the pharmaceutical storage state display.

In this processing, first the controller 222 performs initialization processing (S1801 in FIG. 18). The settings discussed below (management temperature exceedance amount, caution temperature exceedance amount, calculated exceedance amount, set displacement amount, etc.) are cleared in this initialization processing.

Next, the controller 222 determines whether or not all of the measured values have been checked (S1802). The phrase "all of the measured values" here means all of the measured values within each unit of time to be plotted, when the measured values are plotted once every hour, for instance. In this embodiment, as an example, the measured values are plotted once every hour (that is, this is done for 24 hours to produce a day's worth of data). FIG. 18 shows the processing on the measured values in the plot time (here, one hour). The controller 222 proceeds to step S1803 or S1804 if the checking of the measured values has not ended within the plot time.

When a measured value is first acquired in the plot time, the controller 222 acquires the first measured value (S1803) and proceeds to step S1805.

The second and subsequent times that a measured value is acquired in the plot time, the controller 222 acquires the next measured value (S1804) and proceeds to step S1805.

Of the acquired measured values, the controller 222 stores the highest and lowest temperatures in the memory 224.

The controller 222 determines whether or not an acquired measured value is a measured value within the plot time (S1805), and if it is a measured value within the plot time, the controller 222 proceeds to step S1806, and otherwise goes back to step S1802 to check the next measured value.

The controller 222 then calculates the displacement (absolute value) between the measured value and a reference temperature (20° C. is used here as an example), and stores this result in the memory 224 (S1806).

The controller 222 then determines whether or not a management temperature exceedance amount has been set (S1807). The management temperature exceedance amount indicates the greatest differential from among the differences (absolute values) between the previously acquired and determined measured values and a management temperature range (discussed below).

If the management temperature exceedance amount has been set, the controller 222 determines whether or not the measured value is outside the management temperature range (0° C. to 40° C. is used here as an example) (S1808). The management temperature range is the temperature range that is permitted for storing the pharmaceutical, and is preset as the range between the upper limit value (highest temperature) and lower limit value (lowest temperature) at which damage to the stored pharmaceutical is likely to happen. The above-mentioned reference temperature is set by finding the approximate median value of the management temperature.

If the measured value is determined to be within the management temperature range, the controller 222 goes back to step S1802.

If the measured value is determined to be outside the management temperature range, the controller 222 calculates the difference (absolute value) by which the measured value has exceeded the management temperature range, and sets this differential as calculated exceedance α (S1809). For example, if the measured value is 45° C., it exceeds the 40° C. that is the upper limit value (high temperature side) of the management temperature range. In this case, since the difference from the measured value is 5° C. (absolute value), this is set as the calculated exceedance α. For example, if the measured value is −5° C., it is under the 0° C. that is the lower limit value (low temperature side) of the management temperature range. In this case, too, since the difference from the measured value is 5° C. (absolute value), this is set as the calculated exceedance α.

The controller 222 compares the calculated exceedance α to the management temperature exceedance amount (S1810). If the calculated exceedance α is greater than the management temperature exceedance amount, this calculated exceedance α is set to the management temperature exceedance amount (S1811), and if the calculated exceedance α is equal to or less than the management temperature exceedance amount, the flow goes back to step S1802.

If the calculated exceedance α was set to the management temperature exceedance amount (S1811), the controller 222 sets this measured value as a value to be plotted (S1812), and goes back to step S1802.

On the other hand, if the management temperature exceedance amount has not been set (S1807), the controller 222 first determines whether or not the measured value is outside the management temperature range (S1813).

If the management temperature exceedance amount has not been set, and it is determined that the measured value is outside the management temperature range, the controller 222 calculates the difference (absolute value) by which the measured value has exceeded the management temperature range, and sets it as the management temperature exceedance amount (S1814).

If a new management temperature exceedance amount has been set (S1814), the controller 222 sets this measured value as the value to be plotted (S1812), and returns to step S1802.

On the other hand, if the management temperature exceedance amount has not been set, and if the measured value is determined to be within the management temperature range, the controller 222 determines whether or not a caution temperature exceedance amount has been set (S1815). The caution temperature exceedance amount indicates the greatest differential from among the differences (absolute values) between the previously acquired and determined measured values and a caution temperature range (discussed below).

If a caution temperature exceedance amount has been set, the controller 222 determines whether or not the measured value is outside the caution temperature range (5° C. to 30° C. is used here as an example) (S1816). The caution temperature range is the range above or below the temperature at which compositional modification of the pharmaceutical (damage) begins, and is preset as a range between the upper limit value (high temperature side) and lower limit value (low temperature side) at which there is believed to be a risk of damage to the stored pharmaceutical. The lower limit value is set to a temperature at which there is a risk that the pharmaceutical will start to freeze, and is 5° C. in this example, but may instead be 0° C.

If the measured value is determined to be within the caution temperature range, the controller 222 returns to step S1802.

If the measured value is determined to be outside the caution temperature range, the controller 222 calculates the difference (absolute value) by which the measured value has exceeded the caution temperature range, and sets a calculated exceedance β (S1817). For instance, if we let the measured value be 38° C., it exceeds 30° C., which is the upper limit value (high temperature side) of the caution temperature range. In this case, since the difference from the measured value is 8° C. (absolute value), that difference is set as the calculated exceedance β. If we let the measured value be 3° C., it is under 5° C., which is the lower limit value (low temperature side) of the caution temperature range. Here again, since the difference from the measured value is 2° C. (absolute value), that difference is set as the calculated exceedance β.

The controller 222 compares the calculated exceedance β to the caution temperature exceedance amount (S1818). If the calculated exceedance β is greater than the caution temperature exceedance amount, that calculated exceedance β is set to the caution temperature exceedance amount (S1819). If the calculated exceedance β is equal to or less than the caution temperature exceedance amount, the flow returns to step S1802.

When the calculated exceedance β is set to the caution temperature exceedance amount (S1819), the controller 222 sets this measured value as the value to be plotted (S1820), and returns to step S1802.

On the other hand, if the caution temperature exceedance amount has not been set (S1815), the controller 222 first determines whether or not the measured value is outside the caution temperature range (S1812).

If the caution temperature exceedance amount has not been set and it is determined that the measured value is outside the caution temperature range, the controller 222 calculates the difference (absolute value) by which the measured value has exceeded the caution temperature range, and sets this difference as the caution temperature exceedance amount (S1822).

When a new caution temperature exceedance amount has been set (S1822), the controller 222 sets that measured value as the value to be plotted (S1820), and returns to step S1802.

On the other hand, if the caution temperature exceedance amount has not been set and the measured value is within the caution temperature range, the controller 222 proceeds to the processing in FIG. 19.

As shown in FIG. 19, the controller 222 first determines whether or not a set displacement amount has been set (S1901). If no set displacement amount has been set, the controller 222 proceeds to step S1903, and sets the calculated displacement amount calculated in step S1805 in FIG. 18 as the set displacement amount.

If a set displacement amount has been set, the controller 222 compares the set displacement amount to the calculated displacement amount (S1902). If the calculated displacement amount is less than the set displacement amount, the flow returns to step S1802 in FIG. 18. If the calculated displacement amount is greater than the set displacement amount, the calculated displacement amount is set as the set displacement amount (S1903). If a new set displacement amount has been set, the controller 222 sets that measured value as the value to be plotted (S1904), and returns to step S1802 in FIG. 18.

For example, if we let the measured value be 25° C., the calculated displacement amount is the difference of 5° C. between the measured value of 25° C. and the reference temperature of 20° C. If, however, the set displacement amount is 3° C., since the calculated displacement amount is greater than the set displacement amount, this is updated as the set displacement amount (S1903). Also, if we let the measured value be 10° C., the calculated displacement amount is a difference of 10° C. (absolute value) between the measured value of 10° C. and the reference temperature of 20° C. If, however, the set displacement amount (the displacement amount set the last time) is 2° C., the calculated displacement amount is greater than the set displacement amount, so this is updated as the set displacement amount (S1903).

If the calculated displacement amount is equal to the set displacement amount, the controller 222 determines whether the measured value plotted during the previous plot time is on the high temperature side or the low temperature side (S1905). In this case, the measured value obtained by the determination processing prior to the current plot time (hereinafter referred to as the last measured value) is determined to be either higher or lower than the reference temperature.

If the last measured value is on the high temperature side, the controller 222 determines whether or not the current measured value is on the high temperature side (S1906), and if it is, the current measured value is set as the value to be plotted (S1907), and the flow returns to step S1802 in FIG. 18.

On the other hand, if the last measured value is on the low temperature side, the controller 222 determines whether or not the current measured value is on the low temperature side (S1908), and if it is, the current measured value is set as the value to be plotted (S1907), and the flow returns to step S1802 in FIG. 18.

If checking of all of the measured values is finished (S1802), the controller 222 displays a graph of the plotted measured values (discussed below) (S1821).

Display of Pharmaceutical Storage State

FIG. 20 shows examples of the screen 100 displayed on the display component 211 of the portable device 2 as the results of the above processing performed by the controller 222. The various display portions will now be described in the order of their numbering.

FIG. 20a shows the weekly temperature change.

Display area 101: The controller 222 determines whether or not the management temperature exceedance amount has been set during the week that is displayed, and if the management temperature exceedance amount has been set, the day on which the management temperature exceedance amount was greatest is displayed. If no management temperature exceedance amount has been set, it is determined whether or not a caution temperature exceedance amount has been set, and if a caution temperature exceedance amount has been set, the day on which the caution temperature exceedance amount was greatest is displayed. If no management temperature exceedance amount has been set and no caution temperature exceedance amount has been set during the week that is displayed, the day on which the set displacement amount was greatest is displayed. That is, the controller 222 acquires the date on which the temperature displacement width was greatest during the week that is displayed, according to a priority order of management temperature exceedance amount>caution temperature exceedance amount>set displacement amount, from the management temperature exceedance amount, the caution temperature exceedance amount, and the set displacement amount in steps S1811 and S1819 in FIG. 18 and step S1903 in FIG. 19, and displays the result.

Display area 102: Displays the times at which the highest and lowest temperatures were recorded on the day of the greatest temperature displacement width (displayed in the display area 101) during the week being displayed. That is, out of the highest and lowest temperatures acquired and recorded in steps S1803 and S1804 in FIG. 18, the controller 222 acquires and displays the highest and lowest temperatures in a single day. Also, if the acquired highest or lowest temperature in a single day is outside the management temperature range (0 to 40° C.), the display of the high temperature side (here, 38° C. at 1:30 pm) will be displayed in red letters, for example, and the display of the low temperature side (here, 25° C. at 5:30 am) in blue letters, for example. If the results are within the management temperature range but outside the caution temperature range (5 to 30° C.), the display of the high temperature will be in orange, for example, and the display of the low temperature in light blue, for example.

Operation key 103: The user touches this key to switch to the screen in FIG. 23 (discussed below). The screen may be switched not only with a touch key, but also by using a physical button, a menu setting, a flip switch, or the like.

Display area 104: The temperature changes for each day are displayed as bars indicating the highest temperature and the lowest temperature, and these are compiled for one week and displayed as a graph. The high temperature side of the management temperature range is displayed as a red line, for example, and the low temperature side as a blue line, for example, so clearly show the boundary. When the caution temperature range is set, the boundary may be clearly shown by an orange line, for example. The reference temperature may also be displayed. The boundary of each temperature range may be color coded and displayed as a bar.

Operation key 105: The user touches this key to display the previous screen.

Operation key 106: The user touches this key to begin connection with another device such as the pharmaceutical injection device 1, such as near field communication. Consequently, the controller 222 incorporates data about the pharmaceutical temperature management history and so forth into the memory 224, etc.

FIG. 20b is a line graph of the temperature changes in a single day, and shows the screen that is displayed when the user selects a particular day shown in FIG. 20a (or FIG. 23 (discussed below)) by tapping or some other such operation. Some of the display portions that are the same as in FIG. 20a will not be described again.

Display area 108: The selected date is displayed.

Display area 109: The highest and lowest temperatures on the day displayed in the graph (displayed in the display area 108) are displayed along with the times at which they were recorded. If these are outside the management temperature range (0 to 40° C.), the display of the high temperature (here, 38° C. at 1:30 pm) will be displayed in red letters, for example, and the display of the low temperature (here, 25° C. at 5:30 am) in blue letters, for example. If the results are within the management temperature range but outside the caution temperature range (5 to 30° C.), the display of the high temperature will be in orange, for example, and the display of the low temperature in light blue, for example.

Display area 110: A line graph is displayed showing the temperature changes for one day in time series. It is preferable to plot all of the measured temperatures for that day, but since this is impractical, the temperatures with the greatest displacement width from the reference temperature (20° C.) in one hour, for example, may be taken out, and these are plotted for a 24-hour period, as in the processing example in FIGS. 18 and 19. If the displacement width is the same on the high temperature side and the low temperature side, the plot is for the high temperature if the immediately preceding hour was on the high temperature side, and the plot is for the low temperature if it was on the low temperature side. The reference temperature is set to the median value of the management temperature range, but if the median value cannot be set by setting of the caution temperature range (the second temperature range), temperatures closer to the management temperature for the high temperature (or the caution temperature for the high temperature) and the management temperature for the low temperature (or the caution temperature for the low temperature) are each set, and if outside the second temperature range, the measured values that have exceeded most often are plotted. Here again, the boundaries are clearly shown by using a red line, for example, for high temperatures in the management temperature range, and a blue line, etc., for low temperatures. If within the caution temperature range, the boundaries are clearly shown with an orange line, etc. The reference temperature is also displayed.

Operation key 105: The user touches this key to return to the screen in FIG. 20a.

2-2-2. Output of Pharmaceutical Damage Amount

The operation for using the temperature data measured by the pharmaceutical injection device 1 to compute and display the amount of pharmaceutical damage in the pharmaceutical injection device 1 will now be described mainly through reference to FIGS. 21 to 23. The amount of pharmaceutical damage refers to the extent of the effect (damage) by which the pharmaceutical stored in the pharmaceutical injection device 1 is modified by changes in the storage temperature. Also, we shall assume that the temperature data measured by the pharmaceutical injection device 1 is acquired ahead of time with the operation key 106.

Figure 21:
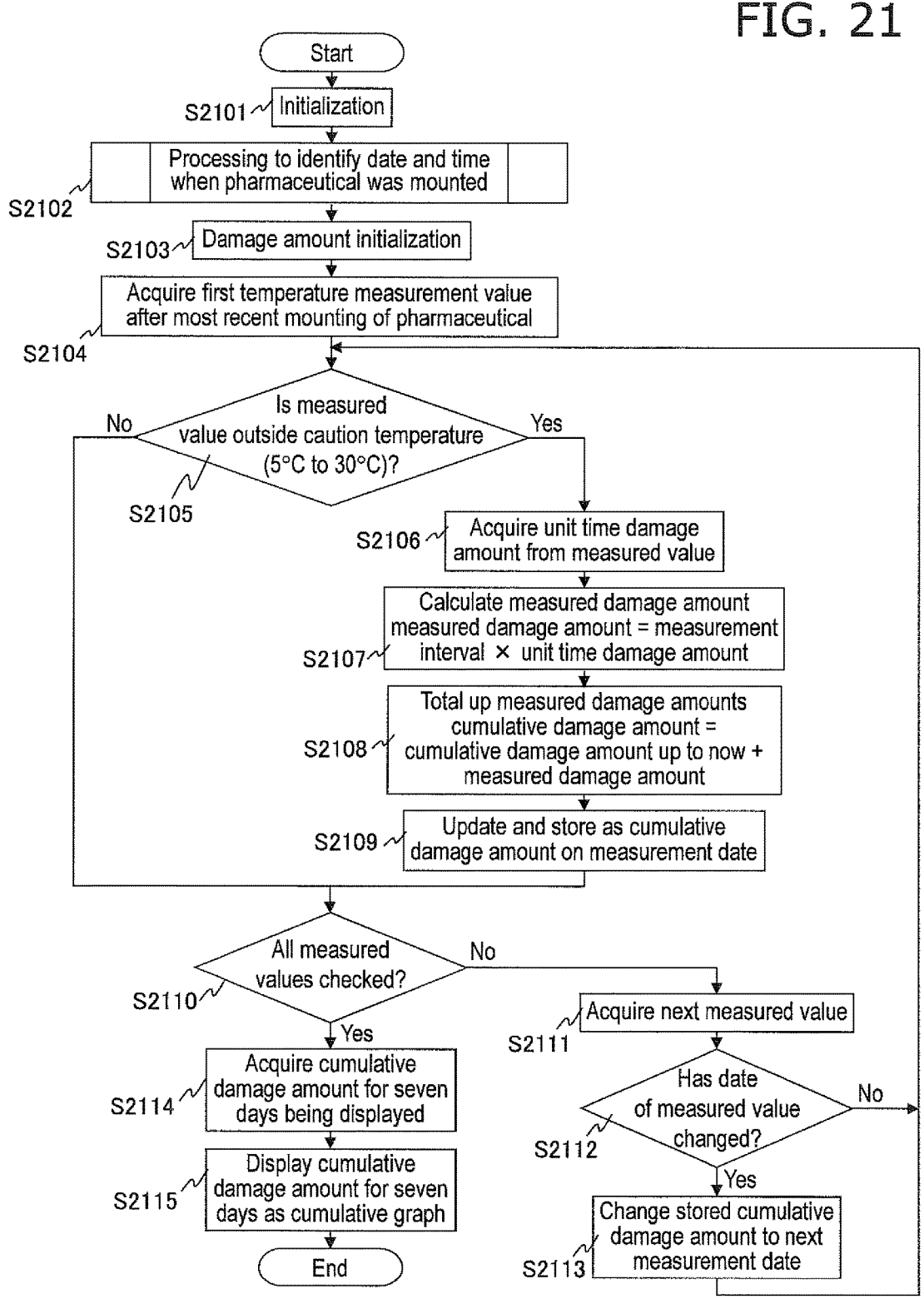
FIG. 21 is an operational flowchart of this portable device.
Figure 22:
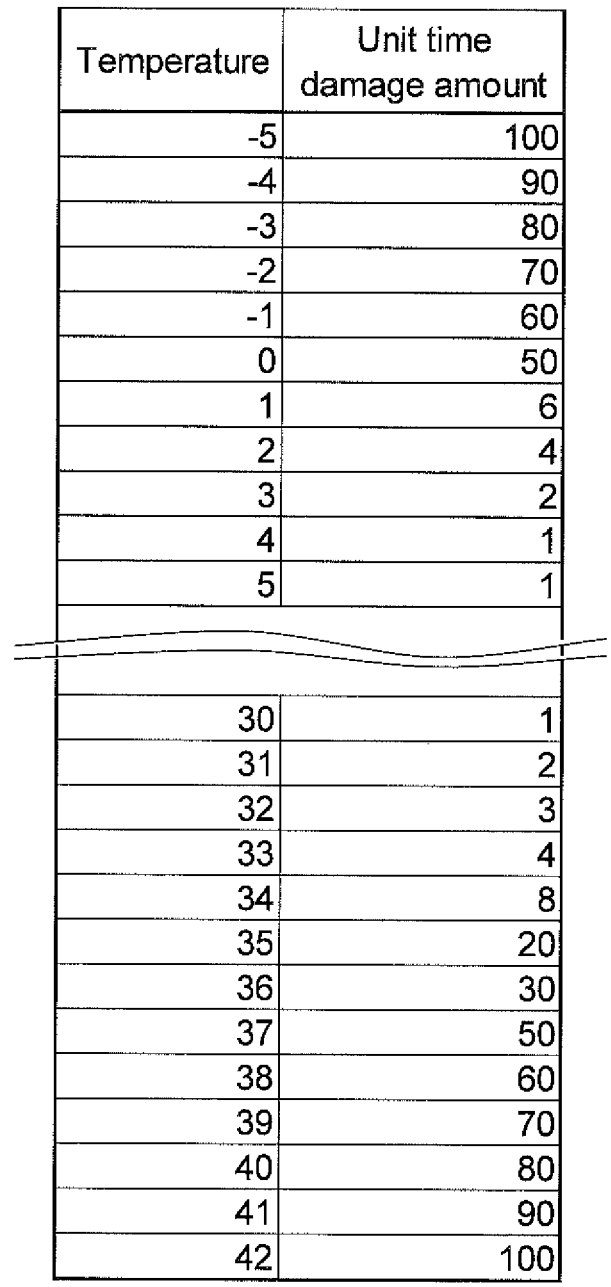
FIG. 22 shows an example of a reference table.

First, the controller 222 of the portable device 2 actuates a specific program and performs initialization processing (S2101 in FIG. 21).

The controller 222 then performs processing to specify the date and time when the pharmaceutical was put in the pharmaceutical injection device 1. Date and time are acquired from the pharmaceutical injection device 1 with connecting the portable device 2 to the pharmaceutical injection device 1 (S2102).

The controller 222 performs initialization if there is a previously acquired damage amount (S2103).

The controller 222 then acquires the first measured value after the most recent mounting of a pharmaceutical, and the measurement date thereof (S2104).

The controller 222 determines whether or not the acquired measured value is outside the caution temperature range (which we will assume here to be 5° C. to 30° C. as an example) (S2105). If no caution temperature range has been set, the determination may be made using the management temperature range (such as 0° C. to 40° C.).

If the measured value is outside the caution temperature range, the controller 222 acquires a unit time damage amount from the measured value (S2106). More specifically, the controller 222 refers to a table stored ahead of time as shown in FIG. 22, and acquires a corresponding unit time damage amount. This unit time damage amount is obtained by making a coefficient of the amount at which the pharmaceutical undergoes modification when allowed to stand for one hour at a certain temperature, and a value of 100 means that the pharmaceutical has completely lost its efficacy due to modification.

The controller 222 calculates the following measured damage amount on the basis of the unit time damage amount (S2107).

measured damage amount=measurement interval× unit time damage amount

Next, the controller 222 totals the measured damage amount as follows, and thereby calculates the cumulative damage amount (S2108).

cumulative damage amount=cumulative damage amount up to last time+measured damage amount this time The controller 222 updates and stores the newly calculated cumulative damage amount as the cumulative damage amount for that measurement date (S2109).

The controller 222 then determines whether or not the damage amount was calculated for all measured values (S2110).

If there are still measured values for which the damage amount has not been calculated, the controller 222 acquires the next measured value (S2111). If the measurement date for the next acquired measured value is the same as the measurement date on which the total was last calculated, the controller 222 goes back to step S2105. If the next measured value has a different measurement date, the measurement date is updated (S2113), and the flow returns to step S2105.

On the other hand, if the damage amount has been calculated for all of the measured values, the controller 222 acquires the cumulative damage amount for the seven days being displayed (S2114), and this cumulative damage amount for the seven days is displayed on the display component 211 as a cumulative graph (described later) (S2115).

Display of Damage Amount

Figure 23:
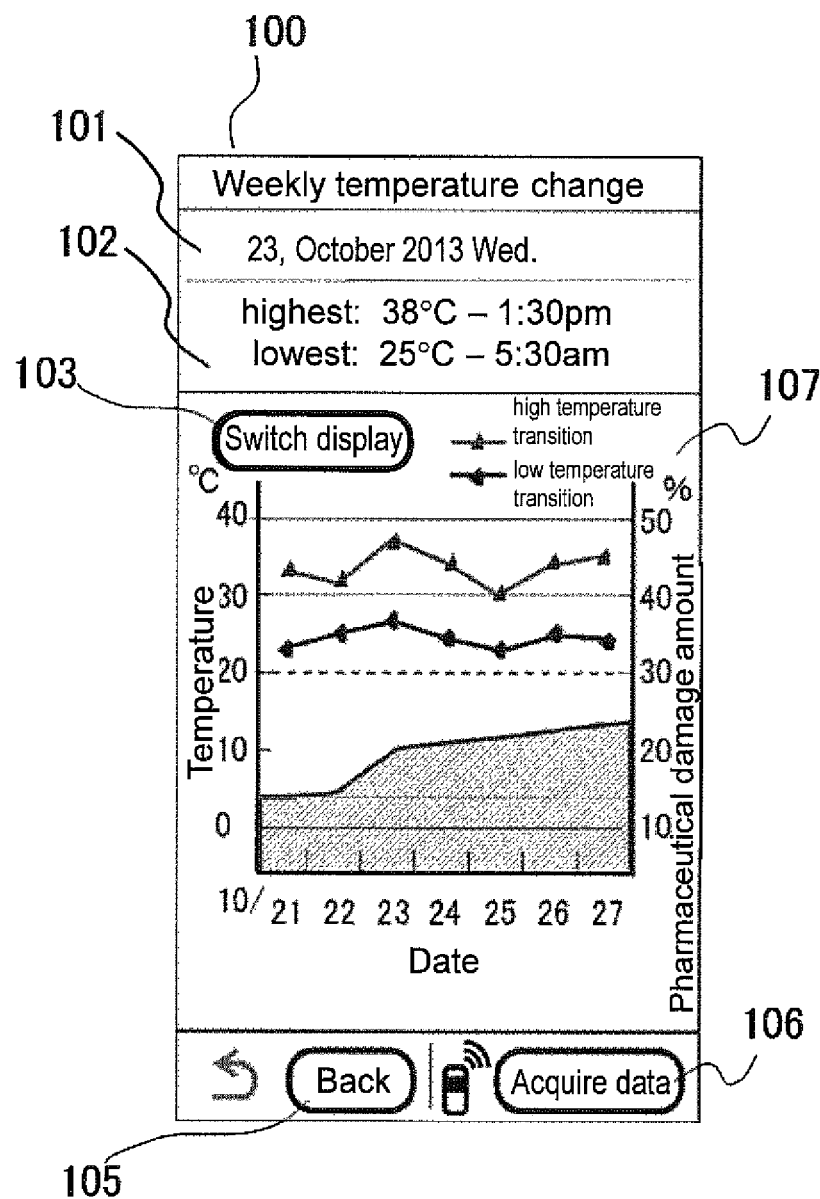
FIG. 23 shows an example of the display screen of this portable device.

FIG. 23 shows an example of the screen 100 displayed on the display component 211 of the portable device 2 as the result of the above-mentioned processing by the controller 222. The user switches from the screen shown in FIG. 20a to this screen by touching the operation key 103. The display portions that are the same as in FIG. 20a will not be described again.

Operation key 103: The user touches this key to switch to the screen shown in the above-mentioned FIG. 20a.

Display area 107: A graph display of the cumulative damage amount for seven days acquired in step S2114 of FIG. 21 is given in this area. The cumulative damage amount, as discussed above, is obtained by assigning a coefficient to the storage temperature at which the pharmaceutical was affected (damaged) by modification, and a pharmaceutical modification rate is calculated as the cumulative amount of damage from how long the pharmaceutical was left at that temperature. One week's worth of damage is displayed as a cumulative graph in addition to the damage amount up to that point. The limit amount of pharmaceutical damage (such as 50% of the damage amount) is displayed as a boundary with a red line, etc. For one week's worth of display, the transition of the highest temperature each day is displayed as a line graph, etc. Similarly, the transition of the lowest temperature each day is displayed as a line graph, etc.

2-3. Modification Example

In the above embodiment, a caution temperature range need not be provided. In this case, the processing of steps S1815 to S1822 is eliminated. Whether or not to provide a caution temperature range can be decided according to the type of pharmaceutical, the usage environment, and so on.

The calculated exceedance α or the calculated exceedance β may also be calculated by the exceedance of the measured value with respect to a reference temperature (such as 20° C.) in place of the difference between the measured value and the management temperature range, or the difference between the measured value and the caution temperature range.

Also, in the above embodiment, the damage amount is calculated by the portable device 2, but the pharmaceutical injection device 1 may compute it and send it to the portable device 2.

Also, in the above embodiment, the boundary display of the limit amounts for the management temperature range, caution temperature range, and damage amount displayed on the screen 100 is done with lines, but may instead involve filling in bars.

2-4. Features, Etc.

As discussed above, with this embodiment, storage temperature data about the pharmaceutical in the pharmaceutical injection device 1 is acquired, and storage temperature data is computed, which allows the information indicating the pharmaceutical storage state or the amount of damage to the pharmaceutical to be outputted.

That is, with this embodiment, the configuration is such that the damage amount caused by temperature during storage or by a storage state in which there is the risk that the pharmaceutical syringe 4 in the main body case 3 may be exposed to high or low temperature is displayed in time series. Accordingly, the user can be cautioned that the storage state of the pharmaceutical is approaching the management temperature or that the pharmaceutical is beginning to be damaged, and can therefore change the storage location of the pharmaceutical injection device 1 or be made more aware of its proper handling. As a result, there will be less damage to the pharmaceutical in the pharmaceutical injection device 1.

Embodiment 3

The pharmaceutical injection device 301 pertaining to Embodiment 3 (an example of a pharmaceutical injection device) will now be described. The same symbols and/or diagrams are referred to for those components and functions that are the same as in Embodiment 1 or 2, and these will not be described again in detail.

The pharmaceutical injection device 301 is a fully automatic type of injector, for example. The pharmaceutical injection device 301 differs from the pharmaceutical injection device 1 pertaining to Embodiment 1 in that it has no cover 13 or cover open/closed sensing switch 30, and thus the temperature with an outside air temperature sensor is constantly being acquired.

The pharmaceutical injection device 301 will now be described through reference to FIGS. 24 to 31.

3-1. Configuration 3-1-1. Pharmaceutical Injection Device

Figure 24:
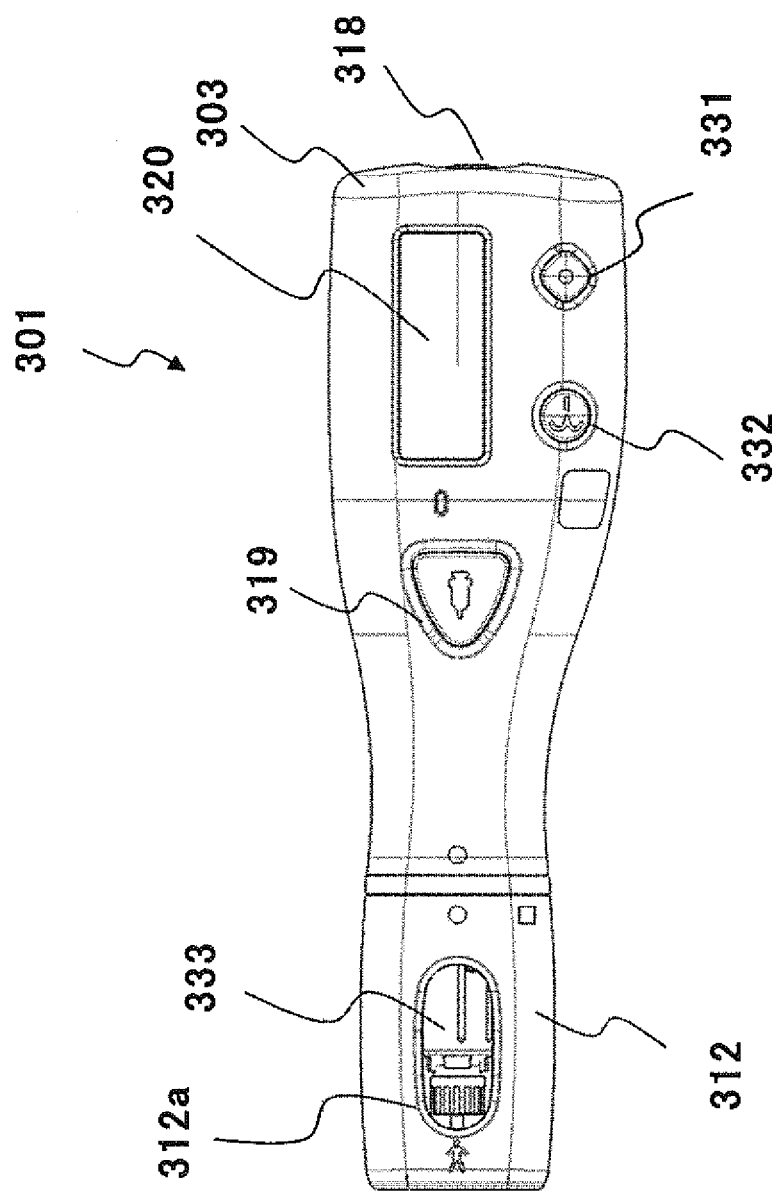
FIG. 24 is an external front view of the pharmaceutical injection device pertaining to Embodiment 3.

As shown in FIG. 24, the pharmaceutical injection device 301 comprises a main body case 303 (an example of a main body case) which is an example of deice main body and a cap 312 that is removably mounted to the front end side of the main body case 303.

The main body case 303 has on its outside a display component 320 (an example of a display component), an air bleed button 332, a complete button 331, a power button 318, and an inject button 319. The display component 320 is disposed on the front face side of the main body case 303. The air bleed button 332 and the complete button 331 are located near the display component 320. The power button 318 is located at the rear end of the main body case 303 (the opposite end from the cap 312). The inject button 319 is located to one side of the display component 320, on the front face side of the main body case 303.

The cap 312 is removably mounted to the distal end side of the main body case 303. The cap 312 is provided with a check window 312a on this front face side so that the interior is visible.

As shown in FIG. 1, the check window 312a is formed so that the interior of the cap 312 is visible, and allows the user to see a syringe cover 333 of a pharmaceutical syringe 304 mounted inside.

Figure 25:
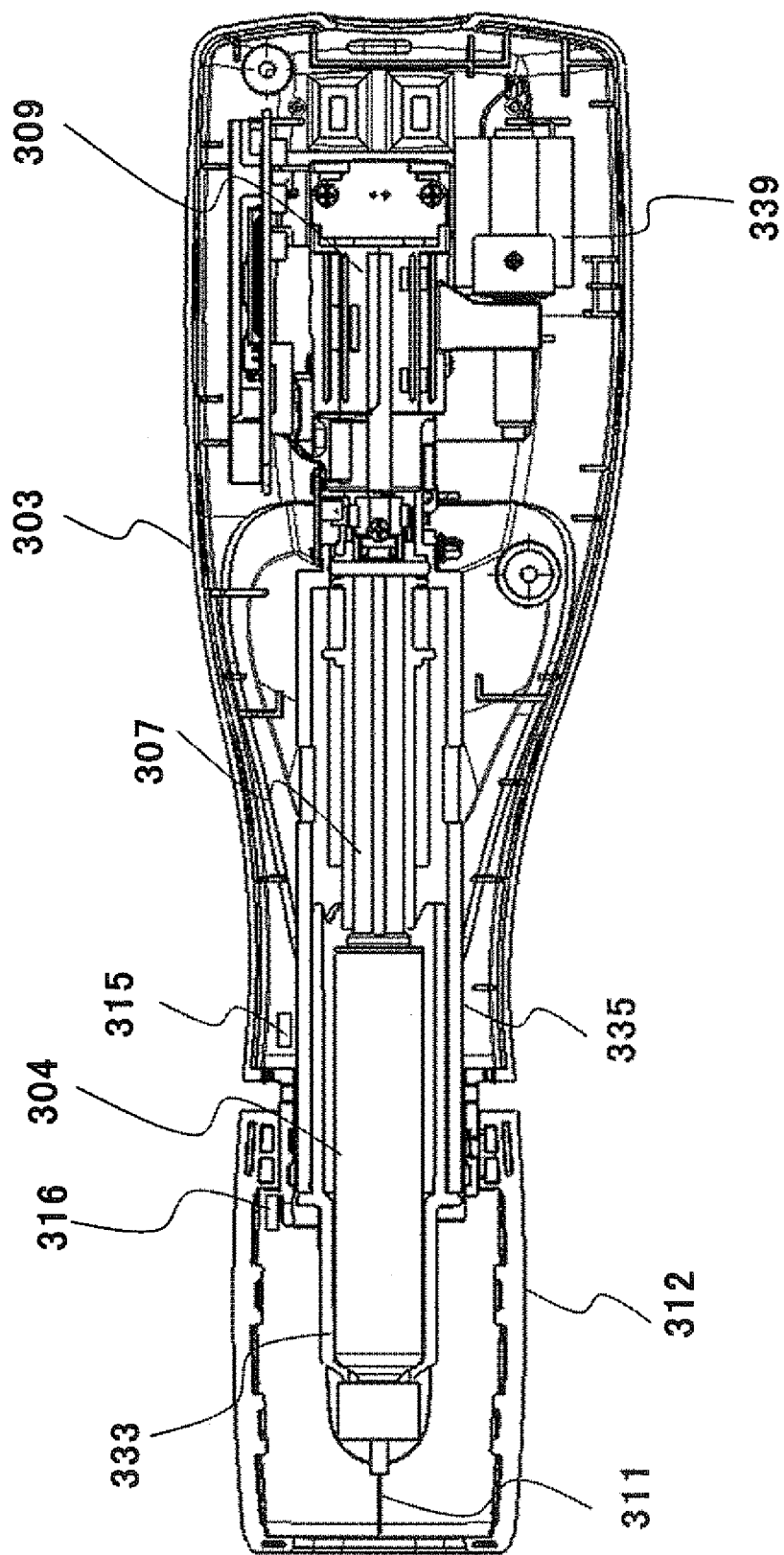
FIG. 25 is an internal front view of the same.

As shown in FIG. 25, the pharmaceutical injection device 301 further comprises an inner case 335 that is movably mounted inside the main body case 303, the pharmaceutical syringe 304 that is mounted on the front end side (the syringe needle mounting side) of the inner case 335, an inside air temperature sensor 315 (an example of an inside air temperature sensor), an outside air temperature sensor 316 (an example of an outside air temperature sensor), a piston 307, and a piston drive motor 309 and a slide motor 339 (an example of a drive mechanism) as a drive means.

The pharmaceutical syringe 304 is inserted into the inner case 335 and mounted to the inner case 335. The piston drive motor 309 drives the piston, and the slide motor 339 is used to drive needle insertion and removal.

The outside air temperature sensor 316 is disposed at a location on the outer peripheral face of the distal end portion of the main body case 303, near the portion where the cap 312 is mounted, that is, at a location near the mounting position of the pharmaceutical syringe 304. Accordingly, the outside air temperature sensor 316 is located so that it is usually in contact with the outside air.

The inside air temperature sensor 315 is provided inside the main body case 303, such as on the outside of the inner case 335 and at a position near where the pharmaceutical syringe 304 is mounted. The inside air temperature sensor 315 is disposed in a space that is blocked off from the outside air in the main body case 303.

3-1-2. Control Circuit

Figure 26:
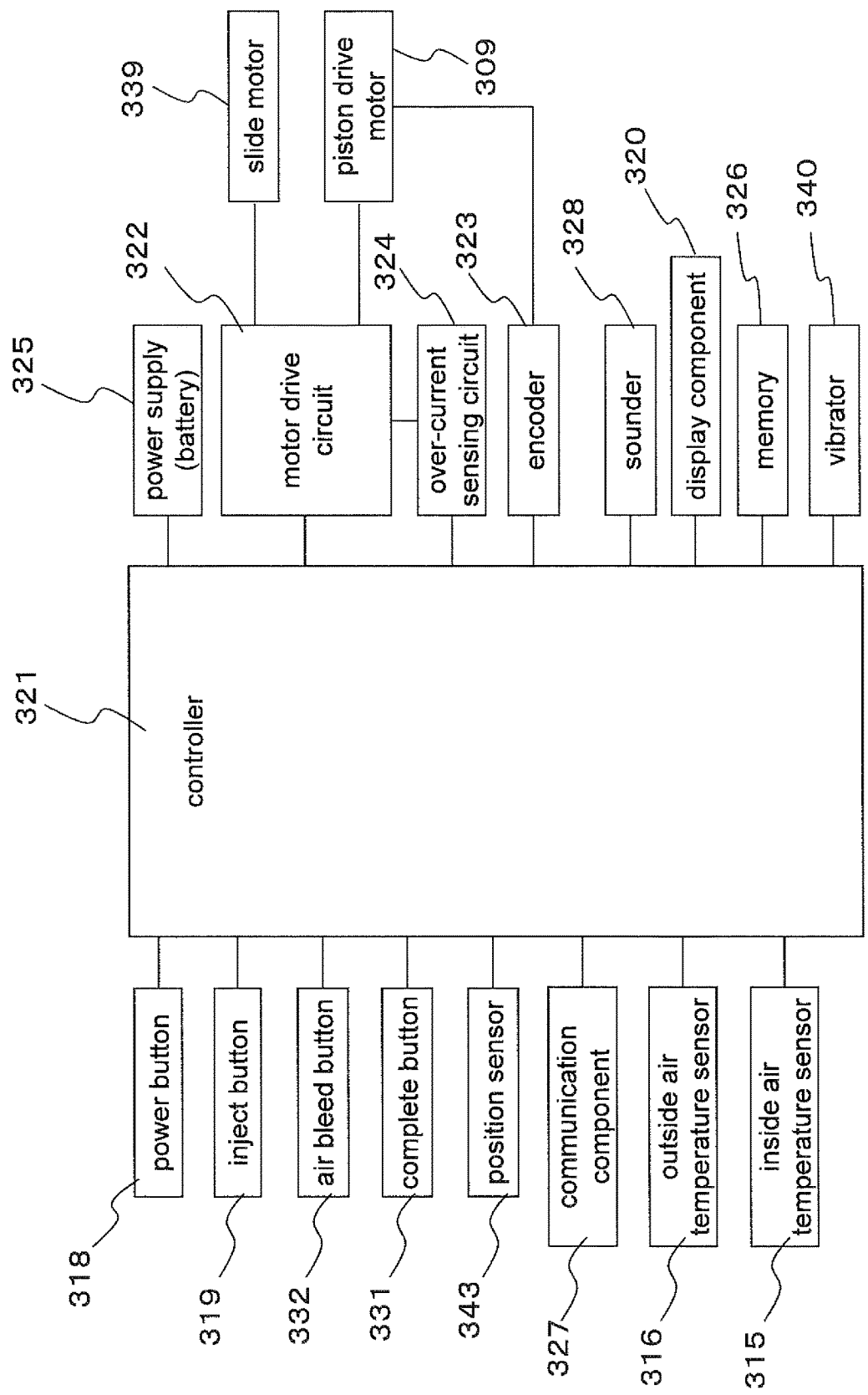
FIG. 26 is a control block diagram of the same.
Figure 27:
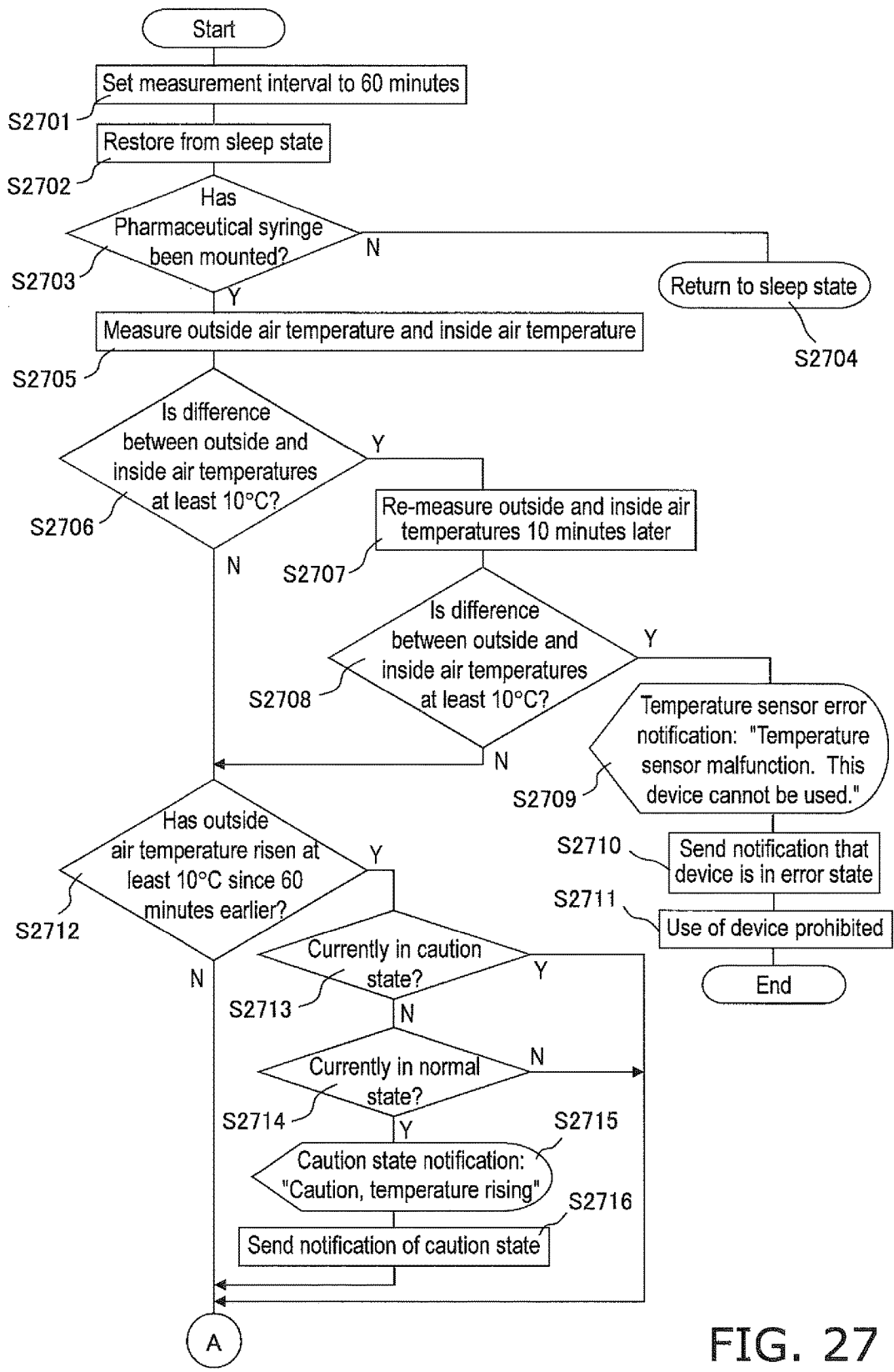
FIG. 27 is an operational flowchart of the same.

FIG. 26 is a block diagram of the control circuit of the pharmaceutical injection device 301 pertaining to this embodiment, and of the surrounding configuration. In FIG. 26, a controller 321 is connected to a charging circuit or other such power supply (battery) 325. The controller 321 is further connected to the above-mentioned power button 318, the air bleed button 332, the complete button 331, the inject button 319, the display component 320, a sounder 328 that outputs a sound (such as a buzzer), and a vibrator 340 having a vibration function. The controller 321 is also connected to a motor drive circuit 322. The motor drive circuit 322 inputs signals from an over-current sensing circuit 324 that monitors the motor current, a position sensor 343 that senses the position of the piston 307, and an encoder 323 that monitors the rotation of the motor. The motor drive circuit 322 controls the drive of the piston drive motor 309 and of the slide motor 339, which moves the needle in and out of the skin.

Furthermore, the controller 321 is connected to the position sensor 343 that is used to sense the position of the piston 307 and the mounting state of a needle 311 and/or the pharmaceutical syringe 304 to the inner case 335.

The controller 321 includes a CPU or other such processor. The controller 321 reads a specific computer program for executing a pharmaceutical storage operation (discussed below) or other operation of the pharmaceutical injection device 301 from a memory 326, and executes the program.

3-2. Operation 3-2-1. Pharmaceutical Injection Operation

With the pharmaceutical injection device 301 pertaining to this embodiment, first the user presses the power button 318, points the cap 312 side up, and presses the air bleed button 332. This starts the air bleed operation.

When the mounting of the pharmaceutical syringe 304 and the needle 311 is sensed by the controller 321 via the position sensor 343, the slide motor 339 moves the entire inner case 335 to the front end side of the main body case 303. This causes the tip of the needle 311 to stick out forward past the opening of the cap 312. After this, if the piston drive motor 309 moves the piston 307 to the front side, the front end of this piston 307 pushes on the rear end of the pharmaceutical syringe 304. Consequently, part of the pharmaceutical in the pharmaceutical syringe 304 flows out from the tip of the needle 311, and air is bled from inside the pharmaceutical syringe 304 and the needle 311. After this, when the user presses the complete button 331, the slide motor 339 is rotated backward to a specific value, and the inner case 335 is returned to its original position. The inner case 335 may also be returned to its original position automatically, without pressing the complete button 331.

Once the air bleed operation is complete, the flow moves on to the pharmaceutical injection operation. The cap 312 of the pharmaceutical injection device 301 is placed against the injection site of a body (a person's skin, etc.), and in this state the user presses the inject button 319, whereupon the entire inner case 335 is moved by the slide motor 339 to the front end side of the main body case 303. This causes the tip of the needle 311 to stick out forward past the opening of the cap 312, and the needle 311 pierces the skin (piercing state).

After this, the piston drive motor 309 moves the piston 307 to the front side, whereupon the front end of this piston 307 pushes on the rear end of the pharmaceutical syringe 304. This causes a specific amount of the pharmaceutical in the pharmaceutical syringe 304 to be injected from the tip of the needle 311 into the body.

When the specified injection of the pharmaceutical is then completed, the controller 321 of the pharmaceutical injection device 301 reverses the slide motor 339 through the motor drive circuit 322. This retracts the inner case 335 and removes the needle 311 from the body (retracted state).

This completes the pharmaceutical injection operation of the fully-automatic pharmaceutical injection device 301.

3-2-2. Pharmaceutical Storage Operation

In addition to the above-mentioned pharmaceutical injection operation, the pharmaceutical injection device 301 also executes the following pharmaceutical storage operation. In this pharmaceutical storage operation, just as in Embodiment 1, the pharmaceutical storage temperature is measured by the inside air temperature sensor 315 and the outside air temperature sensor 316, and device control and information generation and output are executed according to the measurement results. The pharmaceutical storage operation of the pharmaceutical injection device 301 pertaining to this embodiment will now be described through reference to FIGS. 27 to 31.

The pharmaceutical injection device 301 automatically goes into a standby state, that is, a sleep state, when no pharmaceutical injection operation is being performed. In this sleep state, no temperature measurement is executed by the inside air temperature sensor 315 or the outside air temperature sensor 316. The controller 321 performs timer interrupt processing at regular time intervals, and executes temperature measurement. After the temperature measurement, the controller 321 puts the pharmaceutical injection device 301 back into its sleep state.

The controller 321 sets the measurement interval of the inside air temperature sensor 315 and the outside air temperature sensor 316 to 60 minutes (S2701).

The controller 321 detects when the set timer period (60 minutes) has elapsed, and restores the pharmaceutical injection device 301 from its sleep state to a state in which temperature measurement is possible (S2702).

The controller 321 determines whether or not the pharmaceutical syringe 304 has been mounted to the main body case 303 (S2703). If the pharmaceutical syringe 304 has not been mounted, the pharmaceutical injection device 301 is put back in its sleep state (S2704).

If the pharmaceutical syringe 304 has been mounted to the main body case 303, the controller 321 executes temperature measurement with the inside air temperature sensor 315 and the outside air temperature sensor 316 (S2705).

The controller 321 calculates the difference between the inside air temperature and the outside air temperature acquired from the inside air temperature sensor 315 and the outside air temperature sensor 316, and determines whether or not this temperature difference is at or over 10° C. (S2706).

If the temperature difference is at or over 10° C., the controller 321 again measures the outside air temperature and the inside air temperature 10 minutes later (S2707), calculates the difference between the outside air temperature and the inside air temperature, and determines whether or not this temperature difference is at or over 10° C. (S2708).

If the temperature difference is at or over 10° C., the controller 321 causes the display component 320 to display a message such as "Temperature sensor malfunction. This device cannot be used," as shown in FIG. 31f (S2709).

Here, if the large difference between the outside air temperature and inside air temperature is not resolved, it is very likely that either one of the temperature sensors is malfunctioning, or the pharmaceutical injection device 301 itself is malfunctioning.

Thus, the controller 321 informs the portable device 2 (the same as in Embodiments 1 and 2) that the pharmaceutical injection device 301 is malfunctioning (S2710), and also prohibits the use of the pharmaceutical injection device 301 (S2711).

Here, the concept of prohibiting the use of the pharmaceutical injection device 301 means, for example, that the controller 321 halts the operation of the motor drive circuit 322 or other such drive means, or deactivates the switching by the inject button 319, and thereby prohibits the operation of the pharmaceutical injection device 301.

On the other hand, if the controller 321 determines in S2706 or S2708 that the difference between the outside air temperature and the inside air temperature is less than 10° C., it determines whether or not the outside air temperature has risen by 10° C. or more from the time of the previous measurement (here, 60 minutes earlier) (S2712). That is, even if the current outside air temperature is not high, the user can be informed quickly and ahead of time about a worsening of the storage state of the pharmaceutical, by grasping that the outside air temperature is tending to rise.

If the increase is 10° C. or more, the controller 321 determines whether or not the pharmaceutical injection device 301 is currently in a caution state (S2713).

If the pharmaceutical is not currently in a caution state, the controller 321 determines whether or not the pharmaceutical injection device 301 is currently in a normal state (S2714).

If the pharmaceutical injection device 301 is currently in a normal state, the controller 321 performs an operation to caution the user. More specifically, as shown in FIG. 31a, information that urges caution, such as "Caution, temperature rising," is displayed on the display component 320 (S2715).

The controller 321 also sends the same caution notification from a communication component 327 (S2716).

Figure 28:
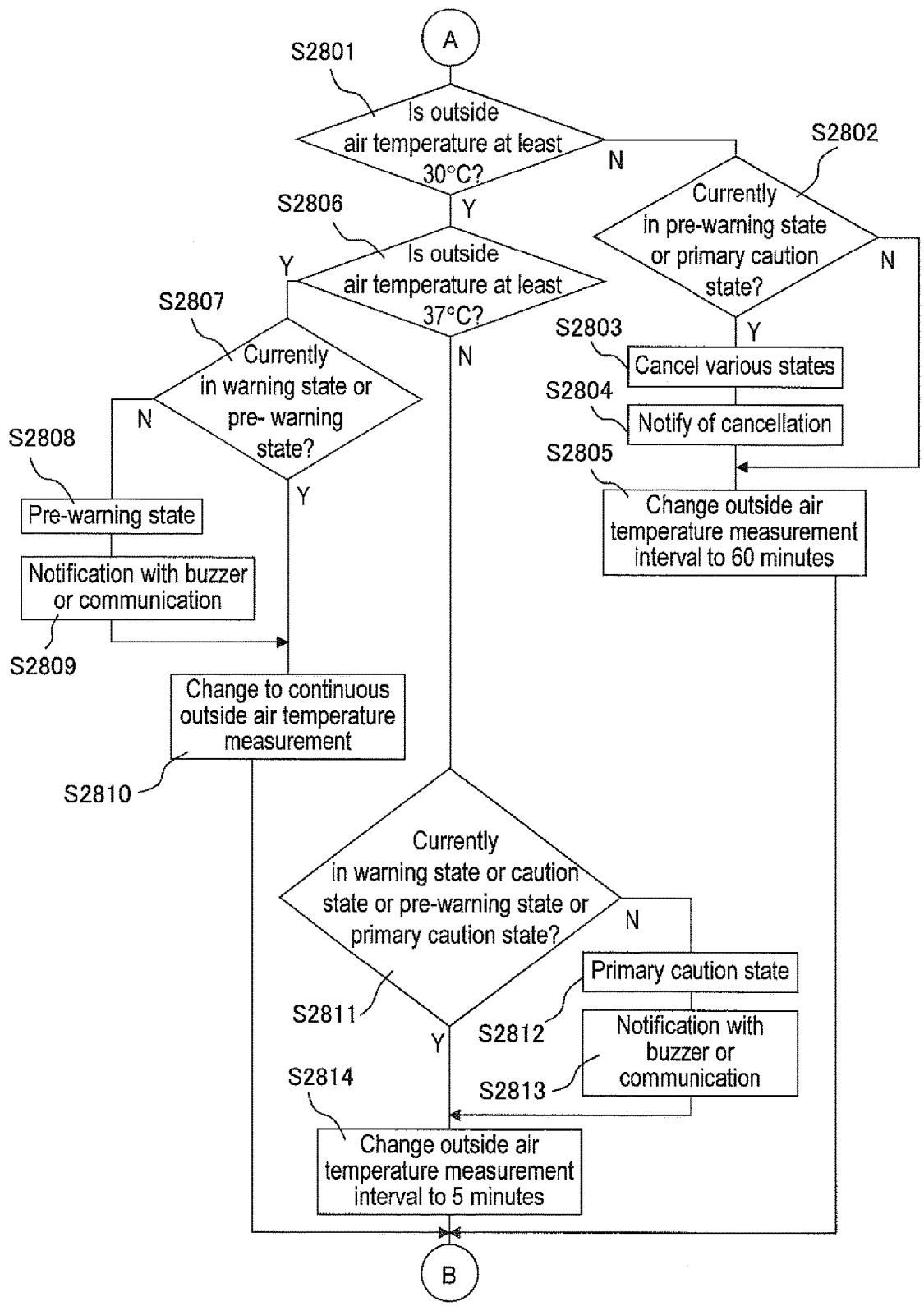
FIG. 28 is an operational flowchart of the same.

If the rise in the outside air temperature in S2712 was not at least 10° C. from the time of the last measurement, or if the pharmaceutical injection device 301 was currently in a caution state in S2713, and if caution notification was performed in S2714, etc., the flow proceeds to S2801 in FIG. 28.

Temperature Sensing by Outside Air Temperature Sensor 316

Next, the temperature sensing done by the outside air temperature sensor 316 will be described through reference to FIG. 28.

In S2801 in FIG. 28, if the temperature sensed by the outside air temperature sensor 316 is not at least 30° C., the controller 321 confirms whether the current state of the pharmaceutical injection device 301 is a "pre-warning state" or a "temporary caution state" (S2802).

If there is a "pre-warning state" or a "temporary caution state" in S2802, since that state has already been exited, the controller 321 cancels the "pre-warning state" or "temporary caution state" (more specifically, the information data or flag for the pre-warning state" and "temporary caution state" stored in the memory 326 is reset) (S2803).

After this, the controller 321 sends a notification that the above-mentioned state ("pre-warning state" or a "temporary caution state") has been cancelled (S2804). More specifically, a display is given on the display component 320 to the effect that the above-mentioned state has been cancelled, or a transmission to the effect that the above-mentioned state has been cancelled is made to the portable device 2 via the communication component 327.

Figure 29:
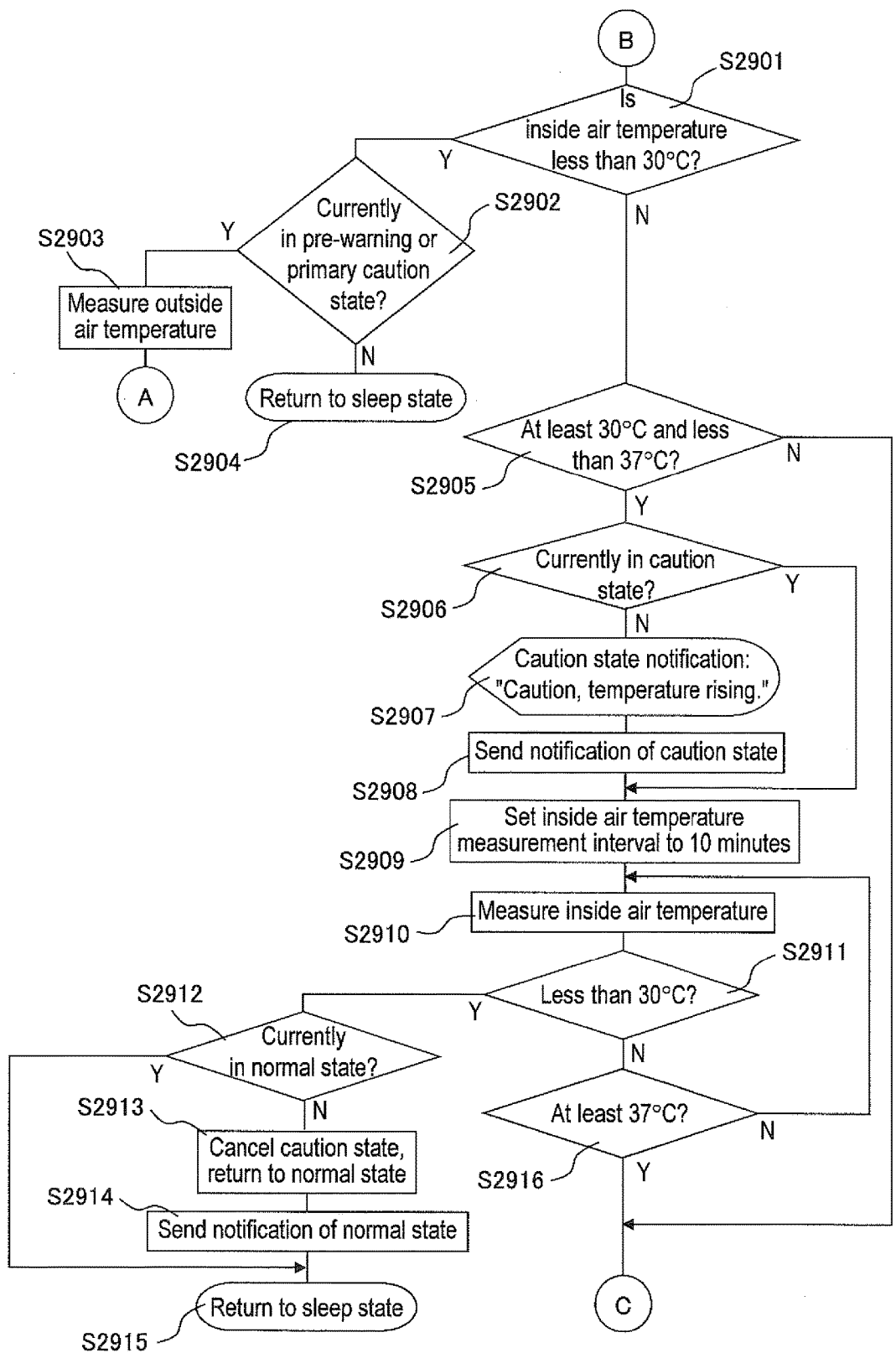
FIG. 29 is an operational flowchart of the same.
Figure 30:
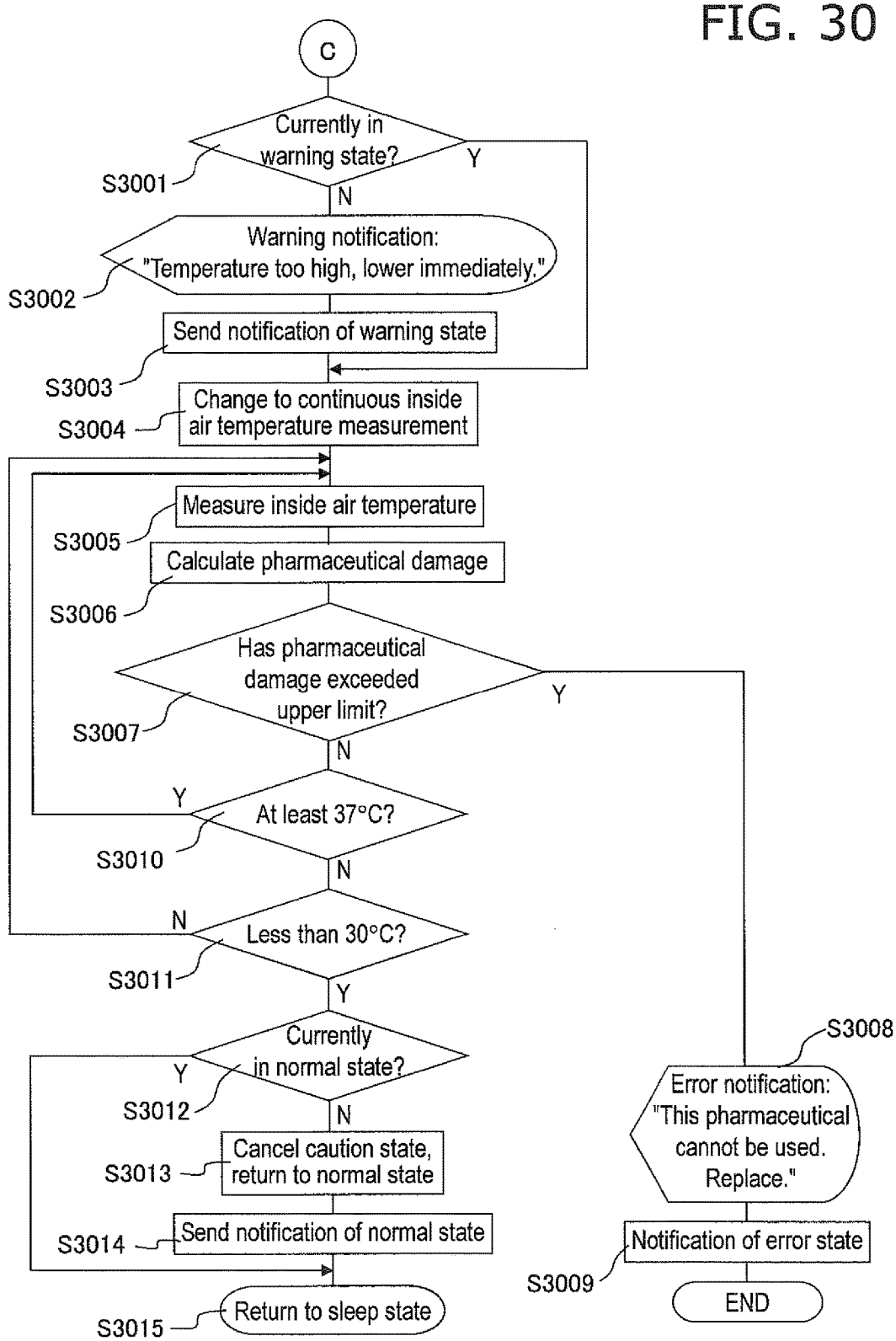
FIG. 30 is an operational flowchart of the same.
Figure 31:
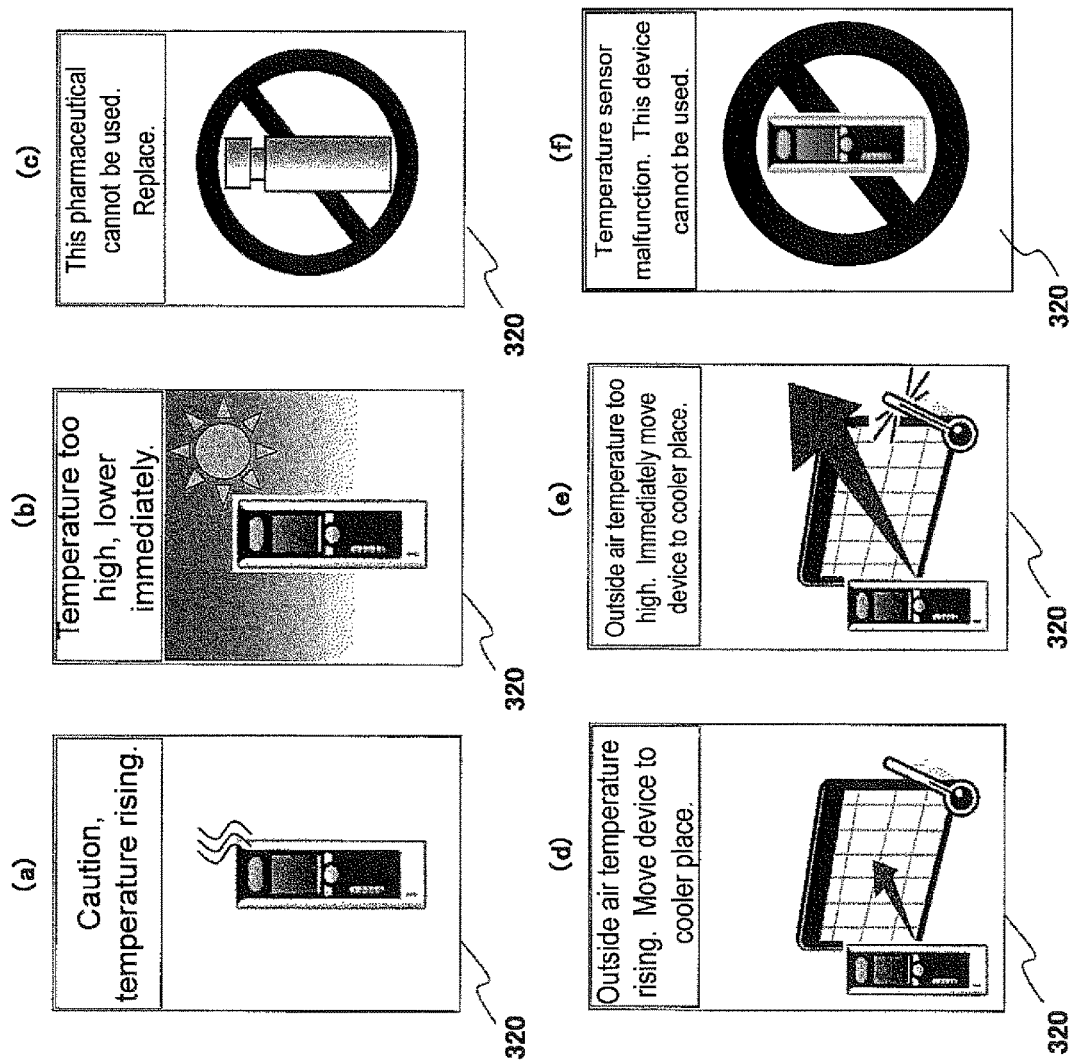
FIG. 31 consists of diagrams of the display component of the same.

The controller 321 then changes the outside air temperature measurement interval to the interval for a normal state (such as an interval of 60 minutes) (S2805), after which the flow moves to S2901 in FIG. 29.

Also, if there is neither a "pre-warning state" nor a "temporary caution state" in S2802, the outside air temperature measurement interval in S2805 is changed to the interval for a normal state (such as an interval of 60 minutes) (S2805), and the flow moves to S2901 in FIG. 29.

On the other hand, if it is determined that the temperature sensed by the outside air temperature sensor 316 is at or over 30° C., the controller 321 determines whether or not the outside air temperature is at or over 37° C. (S2806).

If the outside air temperature is at or over 37° C., the controller 321 confirms whether or not the current state of the pharmaceutical injection device 301 is a "warning state" or a "pre-warning state) (S2807).

If the current state is neither a "warning state" nor a "pre-warning state," the controller 321 sets the "pre-warning state," and causes the display component 320 to display a pre-warning message such as "Outside air temperature too high. Move device immediately to cooler place" as shown in FIG. 31e (S2808). The controller 321 also executes a notification with a buzzer or other such sounder 328, and notifies the portable device 2 of the pre-warning through the communication component 327 (S2809).

After this, the controller 321 changes the outside air temperature measurement to continuous measurement mode (S2810). Also, if the current state of the pharmaceutical injection device 301 is a "warning state" in S2807 above, the controller 321 moves to the processing in S2810, and changes the outside air temperature measurement to continuous measurement mode. After this, the controller 321 moves to S2901 in FIG. 29.

On the other hand, if the outside air temperature measured by the outside air temperature sensor 316 has dropped below 37° C. in S2806, the controller 321 determines whether the current state of the pharmaceutical injection device 301 is a "warning state," a "pre-warning state," a "temporary caution state," or a "caution state" (S2811). If the pharmaceutical injection device 301 is in none of these states, the controller 321 sets the current state to "primary caution state," and as shown in FIG. 31*d* causes the display component 320 to give a primary caution display such as "Outside air temperature rising. Move device to cooler place" (S2812). The controller 321 then executes a notification with a buzzer or other such sounder 328, and sends the portable device 2 a notification through the communication component 327 that the pharmaceutical injection device 301 is in a primary caution state (S2813).

The controller 321 changes (shortens) the outside air temperature measurement interval to 5 minutes (S2814). After this, the controller 321 moves to S2901 in FIG. 29.

Temperature Sensing by Inside Air Temperature Sensor 315

Then the controller 321 executes the following processes on the basis of the temperature measured by the inside air temperature sensor 315.

The controller 321 determines whether or not the inside air temperature measured by the inside air temperature sensor 315 is less than 30° C. (S2901).

If the inside air temperature is less than 30° C., the controller 321 confirms whether the current state of the pharmaceutical injection device 301 is a "pre-warning state" or a "temporary caution state" (S2902).

If the current state is a "pre-warning state" or a "temporary caution state," the controller 321 measures the outside air temperature with the outside air temperature sensor 316 (S2903) and then goes back to S2801 in FIG. 28.

Also, if the current state is neither a "pre-warning state" nor a "temporary caution state" in S2902, the controller 321 returns the pharmaceutical injection device 301 to its sleep state (S2904), and ends processing.

On the other hand, if the inside air temperature is at or over 30° C. in S2901, the controller 321 determines whether or not the inside air temperature is at or over 30° C. and no more than 37° C. (S2905).

If the inside air temperature is at or over 30° C. and less than 37° C., the controller 321 determines whether or not the pharmaceutical injection device 301 is currently in a "caution state" (S2906).

If the current state is not a "caution state," the controller 321 performs an operation to caution the user. More specifically, information that urges caution, such as "Caution, temperature rising" as shown in FIG. 31*a*, is displayed on the display component 320 (S2907).

The controller 321 also sends a similar caution notification from the communication component 327 (S2908).

Here, after being cautioned, the user of the pharmaceutical injection device 301 moves the pharmaceutical injection device 1 into the shade from a situation in which direct sunlight or the like is causing the temperature to rise. As a result, the temperature sensed by the inside air temperature sensor 315 can be lowered, and damage to the pharmaceutical can be suppressed before it happens.

The controller 321 then changes (shortens) the temperature measurement interval by the inside air temperature sensor 315 to 10 minutes (S2909), and executes temperature measurement by the inside air temperature sensor 315 at this measurement interval (S2910).

Next, the controller 321 determines whether or not the measured inside air temperature is lower than 30° C., that is, whether or not the inside air temperature has returned to normal (S2911).

If the inside air temperature is lower than 30° C., the controller 321 determines whether or not the pharmaceutical injection device 301 was in a "normal state" up to now (S2912). In this case, since the pharmaceutical injection device 301 is in a state in which caution is urged, the controller 321 determines that it was not in a "normal state" up to now, deletes the caution display from the display component 320, and returns the pharmaceutical injection device 301 to its normal state (S2913).

The controller 321 then notifies the portable device 2 that the pharmaceutical injection device 301 has entered its "normal state" (S2914), returns the pharmaceutical injection device 301 to its sleep state (S2915), and ends processing.

On the other hand, if the inside air temperature in S2911 is not less than 30° C., that is, if the inside air temperature has not returned to normal, the controller 321 determines whether or not the inside air temperature is at or over 37° C. (S2916), returns to S2910 if the inside air temperature is not at least 37° C., and proceeds to S3001 in FIG. 30 if the inside air temperature is at or over 37° C.

Pharmaceutical Damage Determination

If the inside air temperature is at or over 37° C., the controller 321 determines whether or not the pharmaceutical injection device 301 is currently in a "warning state," which is more urgent than a caution state (S3001).

If the pharmaceutical injection device 301 is determined not to be in a "warning state," the controller 321 causes the display component 320 to give an emergency warning display such as "Temperature too high, lower immediately" as shown in FIG. 31*b* (S3002).

The controller 321 also notifies the portable device 2 from the communication component 327 that the pharmaceutical injection device 301 has entered a "warning state" (S3003). Upon receiving a warning notification, the user of the pharmaceutical injection device 301 moves the pharmaceutical injection device 301 into the shade from a situation in which direct sunlight or the like is causing the temperature to rise, for example. As a result, the temperature sensed by the inside air temperature sensor 315 can be lowered, and damage to the pharmaceutical can be suppressed before it happens.

When the pharmaceutical injection device 301 enters this "warning state," the controller 321 changes the temperature measurement by the inside air temperature sensor 315 to continuous measurement mode (S3004), and executes temperature measurement by the inside air temperature sensor 315 in this continuous measurement mode (S3005).

Next, just as in Embodiment 1, the controller 321 adds up the time during which the temperature was at the warning temperature (such as 37° C.) or higher, computes the pharmaceutical damage amount (S3006), and determines whether or not this total value has exceeded a specific value (pharmaceutical damage upper limit value) (S3007).

If the total value has exceeded the pharmaceutical damage upper limit value, the controller 321 causes the display component 320 to give an error display such as "This pharmaceutical cannot be used. Replace," as shown in FIG. 31*c* (S3008). The controller 321 also notifies the portable device 2 from the communication component 327 that the device is in an error state (S3009), and ends processing.

Here, the controller 321 may put the pharmaceutical injection device 301 in a state in which its use is prohibited. Putting the pharmaceutical injection device 301 in a state in which its use is prohibited here means that the operation of the pharmaceutical injection device 301 is prohibited by the controller 321 by stopping operation of the motor drive circuit 322, or deactivating switching with the inject button 319, for example. This prohibited use state of the pharmaceutical injection device 301 may be cancelled when the mounting of a new pharmaceutical syringe 304 is detected, for example.

On the other hand, if the total value in S3007 has not exceeded a specific value, it is determines whether or not the temperature measured by the inside air temperature sensor 315 is at or over 37° C. (S3010). If the inside air temperature is at or over 37° C., the controller 321 again returns to S3005.

If the inside air temperature is lower than 37° C., the controller 321 determines whether or not this temperature is also lower than 30° C. (S3011). If it is at or over 30° C., the controller 321 again returns to S2905.

If it is lower than 30° C., the controller 321 determines whether or not the pharmaceutical injection device 301 is currently in a "normal state" (S3012).

At this point, as discussed above, since the pharmaceutical injection device 301 is in a state in which a warning has been issued, it is not in a "normal state." Therefore, the controller 321 cancels the warning display from the display component 320, and returns the pharmaceutical injection device 301 to its "normal state" (S3013).

The controller 321 also notifies the portable device 2 through the communication component 327 that the pharmaceutical injection device 301 has entered a "normal state" (S3014).

The controller 321 returns the pharmaceutical injection device 301 that has entered a "normal state" to its sleep state (S3015).

3-3. Features

As discussed above, the pharmaceutical injection device 301 pertaining to this embodiment (an example of pharmaceutical injection device) comprises the main body case 303 (an example of a main body case) in the interior of which can be mounted the pharmaceutical syringe 304 (an example of a pharmaceutical syringe), a drive mechanism that is provided inside the main body case 303 and pushes out the pharmaceutical in the pharmaceutical syringe 304 from the needle 311 (an example of a drive mechanism), the outside air temperature sensor 316 that measures a first temperature that is the temperature outside the main body case 303 (an example of an outside air temperature sensor), the inside air temperature sensor 315 that measures a second temperature that is the temperature inside the main body case 303 (an example of an inside air temperature sensor), the display component 320 (an example of a display component), and the controller 321 that controls the drive mechanism and the display component 320 (an example of a controller). If the first temperature is at or over a specific value, the controller 321 causes the display component 320 to display information about the storage state of the pharmaceutical in the mounted pharmaceutical syringe 304, on the basis of the first temperature.

Specifically, with the pharmaceutical injection device 301, the outside air temperature and the inside air temperature are acquired, and if the outside air temperature is at or over a specific value, the display component 320 displays information about the storage state of the pharmaceutical on the basis of the value of this outside air temperature. The user can grasp ahead of time the storage state of the pharmaceutical corresponding to the outside air temperature, which is affected by the ambient temperature sooner than the temperature in the interior of the main body case 303 (the inside air temperature). Therefore, if there is a risk that the temperature of the pharmaceutical syringe 304 in the main body case 303 will rise, damage to the pharmaceutical can be prevented by changing the storage location before this happens, for example. As a result, damage to the pharmaceutical can be suppressed.

Also, the user can properly grasp the storage state of the pharmaceutical by checking the message sent to the portable device 2, and as a result can prevent damage to the pharmaceutical in the pharmaceutical injection device 301.

Also, the pharmaceutical injection device 301 pertaining to this embodiment differs from that in Embodiment 1 in that no cover is provided to the main body case 303, and there is no need to provide a cover open/closed sensing switch, so the same effect as in Embodiment 1 is obtained with a simpler configuration.

Other Embodiments

Embodiments 1 to 3 were described as examples of the technology disclosed herein, but the technology disclosed herein is not limited to or by these, and can be applied to embodiments involving suitable modifications, substitutions, additions, subtractions, and so forth. Also, the various constituent elements described in Embodiments 1 to 3 above can be combined into new embodiments.

For example, the pharmaceutical injection device 301 pertaining to Embodiment 3 may be communicably connected to the portable device 2 pertaining to Embodiment 2. In this case, just as in Embodiment 2, the portable device 2 performs a pharmaceutical management operation by using stored temperature data (measured values) measured by the inside air temperature sensor 315 and/or the outside air temperature sensor 316 of the pharmaceutical injection device 301 to compute the state of the pharmaceutical stored in the pharmaceutical injection device 301 or the amount of damage thereto.

With the pharmaceutical injection device 301 pertaining to Embodiment 3, information about the storage state of the pharmaceutical may be displayed on the display component on the basis of the outside air temperature and/or the inside air temperature when the outside air temperature and/or the inside air temperature is at or over a specific value.

Also, some or all of the processing of the function blocks in the various embodiments above may be realized by programs. Some or all of the processing of the function blocks in the various embodiments above is then performed by a central processing unit (CPU). Also, the programs for performing this processing are kept on a hard disk, in a ROM, or another such storage device, and are executed in the ROM or read out to a RAM. Also, the various processing of the above embodiments may be realized by hardware, or by software (including an OS (operating system), middleware, or along with a specific library). Mixed processing involving both software and hardware may also be used.

The execution order in the processing methods of the above embodiments is not necessarily limited to what was discussed in the above embodiments, and the execution order can be switched around without departing from the gist of the invention.

INDUSTRIAL APPLICABILITY

Certain implementations can be utilized as a pharmaceutical injection device that injects insulin, a growth hormone, or another such pharmaceutical, for example.

The invention claimed is:
1. A pharmaceutical injection device, comprising:
a main body case, in the interior of which a pharmaceutical syringe can be mounted;

a drive mechanism that is provided inside the main body case and that pushes a pharmaceutical inside the pharmaceutical syringe out of a syringe needle;

a cover that opens and closes an opening on a side of the main body case on which the syringe needle is mounted;

an outside air temperature sensor that measures a first temperature, which is a temperature outside the main body case;

a display component; and a controller that controls the drive mechanism and the display component, and acquires the first temperature at first predetermined intervals, wherein when the cover is closed, the controller causes the display component to display information about a pre-warning or a caution for preventing damage to the pharmaceutical inside of the mounted pharmaceutical syringe when the first temperature measured by the outside air temperature sensor is at or over a first specific value.

2. The pharmaceutical injection device according to claim 1, further comprising a sensor for sensing whether the cover is open or closed, wherein, when the sensor has sensed that the cover is closed, the controller causes the display component to display information about the pre-warning or the caution on the basis of the first temperature.

3. The pharmaceutical injection device according to claim 1, wherein the pre-warning has a higher urgency than the caution, the controller causes the display component to display information about the caution when the first temperature is at least the first specific value and less than a second specific value, and the display component to display the pre-warning when the first temperature is equal to or greater than the second specific value.

4. The pharmaceutical injection device according to claim 1, wherein an outside air measurement opening is provided to the main body case, the outside air temperature sensor is provided to a portion inside the main body case that is opposite the outside air measurement opening, and the outside air measurement opening is opened and closed by the cover.

5. The pharmaceutical injection device according to claim 1, further comprising a communication component that is connected to the controller and is able to communicate with an external device, wherein the controller sends the external device information about a storage state of the pharmaceutical.

6. The pharmaceutical injection device according to claim 1, comprising an inside air temperature sensor that measures a second temperature, which is a temperature inside the main body case, wherein the controller acquires the second temperature at second predetermined intervals, and causes the display component to display information about the pre-warning or the caution on the basis of the second temperature.

7. The pharmaceutical injection device according to claim 6, wherein the inside air temperature sensor is disposed in a space inside the main body case that is blocked off from outside air when the cover is closed.

8. The pharmaceutical injection device according to claim 6, wherein the controller changes the first predetermined interval and the second predetermined interval according to changes in a storage state of the pharmaceutical.

9. The pharmaceutical injection device according to claim 6, wherein the controller causes the display component to display a notification to an effect that the pharmaceutical cannot be used, or the pre-warning or the caution, on the basis of the second temperature.

10. The pharmaceutical injection device according to claim 9, wherein the controller acquires amount of pharmaceutical damage in the mounted pharmaceutical syringe on the basis of cumulative time the pre-warning or the caution is outputted, and causes the display component to display a notification to the effect that the pharmaceutical cannot be used, on the basis of this damage amount.

11. The pharmaceutical injection device according to claim 10, wherein the controller prohibits operation of the drive mechanism according to the damage amount.

12. A pharmaceutical management system, comprising:

the pharmaceutical injection device according to claim 1; and a communication device that is connected so as to be able to communicate with the pharmaceutical injection device, and has a second controller and a second display component, wherein the second controller acquires measured temperature values from the pharmaceutical injection device, produces information indicating a storage state of the pharmaceutical on the basis of these temperature values, and displays the information on the second display component.

13. The pharmaceutical management system according to claim 12, wherein the information indicating the storage state of the pharmaceutical includes a pharmaceutical damage amount calculated on the basis of the temperature values.

14. The pharmaceutical management system according to claim 12, wherein the information indicating the storage state of the pharmaceutical causes the second display component to display information identifying the temperature region in which the pharmaceutical is damaged.

15. A pharmaceutical injection device, comprising:

a main body case, in the interior of which a pharmaceutical syringe can be mounted;

a drive mechanism that is provided inside the main body case and that pushes a pharmaceutical inside the pharmaceutical syringe out of a syringe needle;

an outside air temperature sensor that measures a first temperature, which is a temperature outside the main body case;

an inside air temperature sensor that measures a second temperature, which is a temperature inside the main body case;

a display component; and a controller that controls the drive mechanism and the display component, wherein when the first temperature is at or above a first predetermined value, the controller causes the display component to display information about a pre-warning or a caution for preventing damage to the pharmaceutical inside of the mounted pharmaceutical syringe, on the basis of the first temperature.

16. The pharmaceutical injection device according to claim 15,
wherein the controller further causes the display component to display information about the pre-warning or the caution on the basis of the second temperature.

17. The pharmaceutical injection device according to claim 15,
wherein the controller acquires the first temperature at predetermined intervals, and causes the display component to display a notification to an effect that the device cannot be used, on the basis of difference between the first temperature and the previously acquired first temperature.

18. The pharmaceutical injection device according to claim 15,
wherein the controller prohibits operation of the drive mechanism on the basis of difference between the first temperature and the second temperature.

19. The pharmaceutical injection device according to claim 15,
wherein the controller:
acquires the first temperature at first predetermined intervals,
acquires the second temperature at second predetermined intervals, and
changes the first predetermined interval and the second predetermined interval according to changes in a storage state of the pharmaceutical.

20. The pharmaceutical injection device according to claim 15,
comprising a communication component that is connected to the controller and is able to communicate with an external device,
wherein the controller sends the external device information about a storage state of the pharmaceutical.

21. The pharmaceutical injection device according to claim 15,
wherein the
pre-warning has a higher urgency than the caution, and
the controller causes the display component to display the pre-warning or the caution, or a notification to an effect that the device cannot be used.

22. The pharmaceutical injection device according to claim 21,
wherein the controller acquires amount of pharmaceutical damage in the mounted pharmaceutical syringe on the basis of cumulative time the pre-warning or the caution is outputted, and,
causes the display component to display a notification to the effect that the pharmaceutical cannot be used, on the basis of this damage amount.

23. The pharmaceutical injection device according to claim 22,
wherein the controller prohibits operation of the drive mechanism according to the damage amount.

24. A pharmaceutical management system, comprising:
the pharmaceutical injection device according to claim 15; and
a communication device that is connected so as to be able to communicate with the pharmaceutical injection device, and has a second controller and a second display component,
wherein the second controller acquires measured temperature values from the pharmaceutical injection device, produces information indicating a storage state of the pharmaceutical on the basis of these temperature values, and displays the information on the second display component.

* * * * *